United States Patent
Evans et al.

(10) Patent No.: US 6,333,318 B1
(45) Date of Patent: Dec. 25, 2001

(54) FORMULATIONS USEFUL FOR MODULATING EXPRESSION OF EXOGENOUS GENES IN MAMMALIAN SYSTEMS, AND PRODUCTS RELATED THERETO

(75) Inventors: Ronald M. Evans, La Jolla; Enrique Saez, San Diego, both of CA (US)

(73) Assignee: The Salk Institute for Biological Studies, La Jolla, CA (US)

(*) Notice: Subject to any disclaimer, the term of this patent is extended or adjusted under 35 U.S.C. 154(b) by 0 days.

(21) Appl. No.: 09/079,570

(22) Filed: May 14, 1998

(51) Int. Cl.[7] ............................ A01N 45/00; C12N 15/00; C12N 5/00; C07H 21/02; C07H 21/00

(52) U.S. Cl. ...................... 514/171; 435/320.1; 435/325; 435/455; 536/23.1; 536/23.4

(58) Field of Search .................. 514/44, 171; 435/320.1, 435/325, 455; 424/198.1; 536/23.1, 23.5, 23.4

(56) References Cited

U.S. PATENT DOCUMENTS

| | | | |
|---|---|---|---|
| 4,160,452 | 7/1979 | Theeuwes | 128/260 |
| 4,256,108 | 3/1981 | Theeuwes | 128/260 |
| 4,265,874 | 5/1981 | Bonsen et al. | 424/15 |

(List continued on next page.)

FOREIGN PATENT DOCUMENTS

| | | | |
|---|---|---|---|
| 0 234 944 A1 | 9/1987 | (EP) | C07C/109/10 |
| 0 461 809 A1 | 12/1991 | (EP) | C07C/261/04 |
| WO 89/05345 | 6/1989 | (WO) | C12N/5/00 |
| WO 90/06997 | 6/1990 | (WO) | C12N/15/00 |
| WO 92/05266 | 4/1992 | (WO) | C12N/15/86 |
| WO 92/07573 | 5/1992 | (WO) | A61K/35/12 |
| WO 92/14829 | 9/1992 | (WO) | C12N/15/87 |
| WO 96/37609 | 11/1996 | (WO) | C12N/15/12 |

OTHER PUBLICATIONS

Anderson WF, Nature 392:25–30, 1998.*
Verma et al Nature 389:239–242, 1997.*
Touchette, Nat. Med. 2(1) 7–8, 1996.*
Fahraeus et al J. Pathol. 187:138–146, 1999.*
Kay et al, PNAS 94:12744–12746, 1997.*
Nakagawa et al Steroids 60(5):401–405, 1995.*
Mikitani Biochem. Biophy. Res. Com. 227(2)427–432, 1996.*
Thomas et al (Nature, 362(6419):471–5, 1993.*
*Apoptosis, The Molecular Basis of Cell Death*, Current Communications In Cell & Molecular Biology, Cold Spring Harbor Laboratory Press, 1991.
Bosselman et al., "Replication–Defective Chimeric Helper Proviruses and Factors Affecting Generation of Competent Virus: Expression of Moloney Murine Leukemia Virus Structural Genes via the Metallothionein Promoter" *Molecular and Cellular Biology* 7(5):1797–1806 (1987).
Brent and Ptashne, "A Eukaryotic Transcriptional Activator Bearing the DNA Specificity of a Prokaryotic Repressor," *Cell*, 43:729–736 (1985).

(List continued on next page.)

*Primary Examiner*—Deborah J. R. Clark
*Assistant Examiner*—Sumesh Kaushal
(74) *Attorney, Agent, or Firm*—Foley & Lardner; Stephen E. Reiter

(57) ABSTRACT

In accordance with the present invention, there are provided various methods for modulating the expression of an exogenous gene in a mammalian subject employing modified ecdysone receptors. Also provided are modified ecdysone receptors, as well as homomeric and heterodimeric receptors containing same, nucleic acids encoding invention modified ecdysone receptors, modified hormone response elements, gene transfer vectors, recombinant cells, and transgenic animals containing nucleic acids encoding invention modified ecdysone receptor.

14 Claims, 6 Drawing Sheets

U.S. PATENT DOCUMENTS

| | | | |
|---|---|---|---|
| 4,394,448 | 7/1983 | Szoka, Jr. et al. | 435/172 |
| 4,399,216 | 8/1983 | Axel et al. | 435/6 |
| 4,405,712 | 9/1983 | Vande Woude et al. | 435/5 |
| 4,619,794 | 10/1986 | Hauser | 264/4.1 |
| 4,634,665 | 1/1987 | Axel et al. | 435/68 |
| 4,650,764 | 3/1987 | Temin et al. | 435/240 |
| 4,870,009 | 9/1989 | Evans et al. | 435/70 |
| 4,952,496 | 8/1990 | Studier et al. | 435/91 |
| 4,981,784 | 1/1991 | Evans et al. | 435/6 |
| 4,985,461 | 1/1991 | Hsu et al. | 514/615 |
| 5,024,939 | 6/1991 | Gorman | 435/69.1 |
| 5,071,773 | 12/1991 | Evans et al. | 436/501 |
| 5,117,057 | 5/1992 | Hsu et al. | 564/149 |
| 5,171,671 | 12/1992 | Evans et al. | 435/69.1 |
| 5,198,225 * | 3/1993 | Meybeck et al. | 424/450 |
| 5,225,443 | 7/1993 | Murphy et al. | 514/615 |
| 5,252,479 | 10/1993 | Srivastava | 435/235.1 |
| 5,354,762 | 10/1994 | Hsu et al. | 514/338 |
| 5,399,346 | 3/1995 | Anderson et al. | 424/93.21 |
| 5,424,333 | 6/1995 | Wing | 514/615 |
| 5,654,182 | 8/1997 | Wahl et al. | 435/172.1 |
| 5,677,177 | 10/1997 | Wahl et al. | 435/325 |

OTHER PUBLICATIONS

Christopherson et al., "Ecdysteroid–dependent regulation of genes in mammalian cells by a Drosophila ecdysone receptor and chimeric transactivators" *Proc. Natl. Acad. Sci.USA*, 89:6314–6318 (1992).

Conaway and Conaway, 1994, "Transcription Mechanisms and Regulation", *Raven Press Series on Molecular and Cellular Biology*, vol. 3, Raven Press, Ltd., New York, NY.

Danos et al., "Safe and efficient generation of recombinant retroviruses with amphotropic and ecotropic host ranges" *Proc. Natl. Acad. Sci. USA* 85:6460–6464 (1988).

Devlin et al., "Random Peptide Libraries: A Source of Specific Protein Binding Molecules" *Science*, 249:404–406 (1990).

Evans R.M., "The Steroid and Thyroid Hormone Receptor Superfamily" *Science* 240:889–895 (1988).

Forman et al., "Identification of a Nuclear Receptor That Is Activated by Farnesol Metabolites" *Cell* 81:687–693 (1995).

Freedman et al., "The function and structure of the metal coordination sites within the glucocorticoid receptor DNA binding domain" *Nature* 334:543–546 (1988).

Friedmann, T., "Progress Toward Human Gene Therapy" *Science* 244:1275–1281 (1989).

Furth et al., "Temporal control of gene expression in transgenic mice by a tetracycline–responsive promoter" *Proc. Natl. Acad. Sci. USA* 91: 9302–9306 (1994).

Giguere et al., "Identification of a receptor for the morphogen retinoic acid" *Nature* 330:624–629 (1987).

Glass et al., "The Thyroid Hormone Receptor Binds with Opposite Transcriptional Effects to a Common Sequence Motif in Thyroid Hormone and Estrogen Response Elements" *Cell* 54:313–323 (1988).

Gossen et al., "Control of gene activity in higher eukaryotic cells by prokaryotic regulatory elements" *TIBS* 18:471–475 (1993).

Gossen et al., "Tight Control of gene expression in mammalian cells by tetracycline–responsive promoters" *Proc. Natl. Acad. Sci.* 89:5547–5551 (1992).

Gossen et al., "Transcriptional Activation by Tetracyclines in Mammalian Cells" *Science* 268:1766–1769 (1995).

Green and Chambon, "Nuclear receptor enhance our understanding of transcription regulation" *Trends Genet.* 4:309–314 (1988).

Green and Chambon, "Oestradiol induction of a glucocortiocoid–responsive gene by a chimaeric receptor" *Nature* 325:75–78 (1987).

Harrison, "A structural taxonomy of DNA–binding domains" *Nature* 353:715–719.

Hollenberg and Evans, "Multiple and Cooperative Trans–Activation Domains of the Human Glucocorticoid Receptor" *Cell* 55:899–906 (1988).

Jacobs and Michaels, "Zinc Finger Gene Database" *The New Biologist* 2(6):583 (1990).

Jacobs, G.H., "Determination of the base recognition positions of zinc fingers from sequence analysis" *The EMBO Journal* 11:4507–4517 (1992).

Kamine et al., "Sp1–dependent activation of a synthetic promoter by human immunodeficiency virus type 1 Tat protein" *Proc. Natl. Acad. Sci. USA* 88:8510–8514 (1991).

Keegan et al., "Separation of DNA Binding from the Trascription–Activating Function of a Eukaryotic Regulatory Protein" *Science* 231:699–704 (1986).

Klock et al., "Oestrogen and glucocorticoid responsive elements are closely related but distinct" *Nature* 329:734–736 (1987).

Klug and Rhodes, 'Zince fingers': a novel protein motif for nucleic acid recognition *TIBS* 12:464–469 (1987).

Koelle et al., "The Drosophila EcR Gene Encodes an Ecdysone Receptor, a New Member of the Steroid Receptor Superfamily" *Cell* 67:59–77 (1991).

Kumar and Chambon, "The Estrogen Receptor Binds Tightly to Its Responsive Element as a Ligand–Induced Homodimer" *Cell* 55:145–156 (1988).

Kumar et al., "Functional Domains of the Human Estrogen Receptor" *Cell* 51:941–951 (1987).

Ladias et al., "Regulation of the Apolipoprotein AI Gene by ARP–1, a Novel Member of the Steroid Receptor Superfamily" *Science* 251:561–565 (1991).

Leonard et al., "Charaterization of Somatostatin Transactivating Factor–1, a Novel Homeobox Factor That Stimulates Somatostatin Expression in Pancreatic Islet Cells" *Molecular Endocrinology* 7(10):1275–1283.

Mangelsdorf et al., "The Retinoid Receptors" *The Retinoids: Biology, Chemistry, and Medicine, 2nd Edition* 8:319–349 (1994).

Markowitz, et al. "A Safe Packaging Line for Gene Transfer: Separating Viral Genes on Two Different Plasmids" *Journal of Virology* 61(4):1120–1124 (1988).

Miller et al., "Repetitive zinc–binding domains in the protein transcription factor IIIA from Xenopus oocytes" *The EMBO Journal* 4(6):1609–1614 (1985).

Miller, A. D., "Retrovirus Packaging Cells" *Human Gene Therapy* 1:5–14 (1990).

Miyajima et al. "Identification of two novel members of erbA superfamily by molecular cloning: the gene products of the two are highly related to each other" *Nucleic Acids Research* 16(23): 11057–11074 (1988).

Mlodzik et al., "The Drosophila seven–up Gene, a Member of the Steroid Receptor Gene Superfamily, Controls Photoreceptor Cell Fates" *Cell* 60:211–224 (1990).

Mulligan et al., "Synthesis of rabbit β–globin in cultured monkey kidney cells following infection with a SV40 β–globin recombinant genome" *Nature* 277:108–114 (1977).

Mulligan, R.C., "The Basic Science of Gene Therapy" *Science* 260:926–932 (1993).

Nakamura et al., "DNA Sequence of the Gene for the Outer Membrance Lipoprotein of *E. coli*: an Extremely AT–Rich Promoter" *Cell*, 18:1109–1117 (1979).

No et al., "Ecdysone–inducible gene expression in mammalian cells and transgenic mice" *Proc. Natl. Acad. Sci. USA* 93:3346–3351 (1996).

Perlmann et al., "Determinants for selective RAR and TR recognition of direct repeat HREs" *Genes & Devel.* 7:1411–1422 (1993).

Petkovich et al., "A human retinoic acid receptor which belongs to the family of nuclear receptors" *Nature* 330:444–450 (1987).

Rivera et al., "A humanized system for pharmacologic control of gene expression" *Nature Medicine* 2(9):1028–1032 (1996).

Ross et al. "Targeted expression of a toxin gene to adipose tissue: transgenic mice resistant to obesity" *Genes and Development* 7:1318–1324 (1983).

Scott and Smith, "Searching for Peptide Ligands with an Epitope Library" *Science* 249:386–390 (1990).

Scott et al., "The structure and function of the Homoeodomain" *Biochimica et Biophysica Acta* 989:25–48 (1989).

Severne et al., "Metal binding 'finger' structures in the glucocorticoid receptor defined by site–directed mutagenesis" *EMBO J.* 7(8):2503–2508 (1988).

Shackleford et al., "Construction of a clonable, infectious, and tumorigenic mouse mammary tumor virus provirus and a derivative genetic vector" *Proc. Natl. Acad. Sci. USA* 85:9655–9659 (1988).

Shockett et al., "A modified tetracycline–regulated system provides autoregulatory, inducible gene expression in cultured cells and transgenic mice" *Proc. Natl. Acad. Sci.* 92:6522–6526 (1995).

Sladek et al., "Liver–enriched transcription factor HNF–4 is a novel member of the steroid hormone receptor superfamily" *Genes & Development* 4:2353–2365 (1990).

Spencer et al., "Creating conditional mutations in mammals" *Trends In Genetics* 12(5):181–187.

Strähle et al., "Synergistic action of the glucocortiocoid receptor with transcription factors" *EMBO* 7 (11):3389–3395 (1988).

Studier et al., "[6] Use of T7 RNA Polymerase to Direct Expression of Cloned Genes" *Methods in Enzymology* 185:60–89 (1990).

Thompson and Evans, "Trans–activation by thyroid hormone receptors: Functional parallels with steroid hormone receptors" *Proc. Natl. Acad. Sci. U.S.A.* 86:3494–3498 (1989).

Umesono and Evans, "Determinants of Target Gene Specificity for Steroid/Thyroid Hormone Receptors" *Cell* 57:1139–1146 (1989).

Umesono et al., "Retinoic acid and thyroid hormone induce gene expression through a common responsive element" *Nature* 336:262–265 (1988).

Underhill et al., "Constitutively Active Retinoid Receptors Exhibit Interfamily and Intrafamily Promoter Specificity" *Molecular Endocrinology* 8:274–285 (1994).

Urlaub et al., "Effect of Gamma Rays at the Dihydrofolate Reductase Locus: Deletions and Inversion" *Somatic Cell and Molecular Genetics* 12(6):555–566 (1986).

Wang et al., "COUP transcription factor is a member of the steroid receptor superfamily" *Nature* 340:163–166 (1989).

Watanabe et al., "Construction of a Helper Cell Line for Avian Reticuloendotheliosis Virus Cloning Vectors" *Molecular and Cellular Biology* 3(12):2241–2249 (1983).

Wong et al., "Human GM–CSF: Molecular Cloning of the Complementary DNA and Purification of the Natural and Recombianat Proteins" *Science* 228:810–815 (1985).

Yamamoto, K.R., "Steroid Receptor Regulated Transcription of Specific Genes and Gene Networks" *Ann. Rev. Genet.* 19:209–252 (1985).

Yao et al., "Drosophila ultraspiracle Modulates Ecdysone Receptor Function via Heterodimer Formation" *Cell* 71:63–72 (1992).

Yao et al., "Functional ecdysone receptor is the product of EcR and Ultraspriacle genes" *Nature* 366:476–479 (1933).

* cited by examiner

FORMULATIONS USEFUL FOR MODULATING EXPRESSION OF EXOGENOUS GENES IN MAMMALIAN SYSTEMS, AND PRODUCTS RELATED THERETO

FIELD OF THE INVENTION

The present invention relates to methods in the field of recombinant DNA technology, and products related thereto. More particularly, the invention relates to methods and products for modulating the expression of exogenous genes in mammalian systems.

BACKGROUND OF THE INVENTION

The steroid/thyroid hormone receptors comprise a superfamily of ligand-dependent transcription factors that play a crucial role in mediating changes in cell fate and function (Evans, R. M., Science 240:889–895 (1988)). The receptors transduce extracellular hormonal signals to target genes that contain specific enhancer sequences referred to as hormone response elements (HREs) Evans, (1988); Green and Chambon, Trends Genet. 4:309–314 (1988); Yamamoto, K. R., Annu. Rev. Genet. 19:209–252 (1985)). Each receptor recognizes its own HRE, assuring that a distinct response is triggered by each hormonal signal. Together the collection of related transcription factors and their cognate response elements provides a unique opportunity to control gene expression.

The DNA binding domain of each member of the steroid/thyroid hormone superfamily of receptors has 66–68 amino acids. Twenty of these, including nine cysteines, are conserved throughout the family. The modular structure of members of this receptor superfamily allows the exchange of homologous domains between receptors to create functional chimeras. This strategy was used to demonstrate that the DNA binding domain is solely responsible for the specific recognition of the HRE in vivo (Green and Chambon, Nature 325:75–78 (1987); Giguére et al., Nature 330:624–629 (1987); Petkovich et al., Nature 330:444–450 (1987); Kumar et al., Cell 51:941–951 (1987); Umesono et al., Nature 336:262–265 (1988); Thompson and Evans, Proc. Natl. Acad. Sci. U.S.A. 86:3494–3498 (1989) and in vitro (Kumar and Chambon, Cell 55:145–156 (1988)). By analogy with the proposed structure for Xenopus transcription factor IIIA (Miller et al., EMBO J. 4:1609–1614 (1985)), the invariant cysteines are thought to form two "zinc finger" that mediate the DNA binding function (Hollenberg and Evans, Cell 55:899–906 (1988)). Involvement of these cysteines in Zn(II) coordination is supported by extended X-ray absorption fine structure (Freedman et al., Nature 334:543–546 (1988)), and by the effect of point mutagenesis experiments on DNA binding (Hollenberg and Evans, (1988)); Severne et al., EMBO J. 7:2503–2508 (1988)).

The HREs are in fact structurally related but functionally distinct. The glucocorticoid receptor response element (GRE), estrogen receptor response element (ERE), and thyroid hormone receptor response element (TRE) have been characterized in detail. These particular response elements have been found to have a palindromic pair of hexameric "half-sites" (Evans, (1988); Green and Chambon, (1988)). With optimized pseudo- or consensus response elements, only two nucleotides per half-site differ between GRE and ERE (Klock et al., Nature 329:734–736 (1987)). On the other hand, EREs and TREs have identical half-sites but the number of nucleotide spacers between the two half sites is different (Glass et al., Cell 54:313–323 (1988)).

In contrast to response elements having the palindromic sequence motif, the following hormone receptors typically recognize response elements having two half-sites in a direct-repeat (DR) sequence motif: RXR, RAR, COUP-TF, PPAR, and the like (see, e.g., Mangelsdorf et al., The Retinoids: Biology, Chemistry, and Medicine, 2nd Edition, Raven Press, Ltd., New York, 1994, Chapter 8). Thus at least three distinct means are used to achieve HRE diversity: 1) binding site specificity for a particular half-site; 2) nucleotide spacing between the two half-sites; and 3) the orientation of the half-sites to one another.

In insect systems, a pulse of the steroid hormone ecdysone triggers metamorphosis in Drosophila melanogaster showing genomic effects, such as chromosomal puffing, within minutes of hormone addition. Mediating this response in insects is the functional ecdysone receptor, a heterodimer of the ecdysone receptor (EcR) and the product of the ultraspiracle gene (USP) (Yao et al. (1993) Nature 366:476–479; and Yao et al. (1992) Cell 71:63–72). Responsiveness to an insect ecdysteroid can be recreated in cultured mammalian cells by co-transfection of EcR, USP, an ecdysone responsive reporter, and treatment with ecdysone or the synthetic analog muristerone A.

The ability to manage the expression of genes introduced into mammalian cells and animals would further advance many areas of biology and medicine. For instance, methods that allow the intentional manipulation of gene expression would facilitate the analysis of genes whose gene products cannot be tolerated constitutively or at certain stages of development. Such methods would also be valuable for clinical applications such as gene therapy protocols, where the expression of a therapeutic gene must be regulated in accordance with the needs of the patient (Saez et al. (1997) Current Opinion in Biotechnology 8:608–616). However, to be of broad benefit, gene regulation techniques must allow for rapid, robust and precise induction/repression of gene activity. Precise control of gene expression is an invaluable tool in studying, manipulating and controlling development and other physiological processes.

Early designs to direct gene expression in mammals were based on endogenous elements, such as cytokine response elements or heat-shock proteins. Due to a high level of basal expression in the uninduced state, and pleiotropic effects brought about by general inducing agents, these systems lack the specificity required to regulate genes in mammalian cells and organisms. (Saez et al., supra)

As another means for controlling gene expression in a mammalian system, an inducible tetracycline regulated system has been devised and utilized in transgenic mice, whereby gene activity is induced in the absence of the antibiotic and repressed in its presence (see, e.g, Gossen et al. (1992) Proc. Natl. Acad. Sci. 89:5547–5551; Gossen et al.(1993) TIBS 18:471–475; Furth et al. (1994) Proc. Natl. Acad. Sci. 91:9302–9306; and Shockett et al. (1995) Proc. Natl. Acad. Sci. 92:6522–6526). However, problems were noticed during the development of this system including toxicity of the tetracycline transactivator protein, the requirement for continuous treatment of tetracycline to repress expression, and the slow clearance of antibiotic from bone which interferes with quick and precise induction. While this system has been improved by the recent identification of a mutant tetracycline repressor which acts conversely as an inducible activator, the pharmacokinetics of tetracycline may hinder its use during development when a precise and efficient "on-off" switch is essential (Gossen et al. (1995) Science 268:1766–1769).

Another approach to regulate gene expression relies on induction of protein dimerization, a method derived from studies on the mechanism of action of immunosuppressive agents (Spencer, DM, (1996) *Trends Genet,* 12:181–187). Compounds such as FK506 and cyclosporin A (CsA) subdue the immune response by binding with high affinity to the immunophilins FKBP12 and cyclophilin (CyP), respectively. Using a synthetic homodimer of FK506 (called FK10102), a general strategy was devised to bring together any two peptides, by endowing them with the domain of FKBP12 to which FK506 binds. By chemically linking FK506 and CsA, a heterodimer molecule that can selectively connect two different immunophilin domains and their respectively attached peptides was also generated.

The resulting heterodimerizer, FKCsA, has been used to reconstitute a functional transcription factor by joining a GAL4 DNA-binding domain fused to FKBP12, and the transactivation moiety of VP16 bound to CyP. In cells expressing these chimeric proteins, the expression of a promoter containing GAL4 binding sites was strongly stimulated in the presence of this 'chemical inducer of dimerization' (CID) FKCsA.

The immunosuppressive drug rapamycin is a natural heterodimerizer that complexes with FKBP12 and FKBP12-rapamycin-associated protein (FRAP). A new inducible system based on rapamycin builds on the modularity of mammalian transcription factors and the heterodimerizing properties of this drug (Rivera et al. (1996), *Nat Med* 2:1028–1032). Unfortunately, the attractive pharmacokinetics of this drug are compromised by its effects on the immune system, i.e., rapamycin is incapable of regulating gene expression at doses that are not immunosuppressive.

Two gene control systems based on components of mammalian steroid hormone receptors have recently been developed (Wang et al. (1994) *PNAS USA* 91:8180–8184, Delort and Capecchi (1996) *Num Gene Ther* 7:809–820). Created independently, these two steroid-based methods are nonetheless virtually identical, i.e, both methods combine a truncated form of the progesterone receptor hormone-binding domain with a yeast GAL4 DNA-binding moiety, and the transactivation domain of the VP16 protein. The mutated progesterone receptor moiety fails to bind progesterone but it retains the ability to bind the progesterone and glucocortioid antagonist mifepristone (RU486), such that in the presence of RU486, the fusion protein (called either GLVP or TAXI) activates transcription through a multimer of the GAL4 DNA-binding site placed upstream of a minimal promoter.

Although these systems represent an improvement over previous hormone based designs, their performance in cells remains poor. In transient and stable transfections of various cell types, a high level of basal activity dampens the level of inducibility of the above-described approaches. Moreover, since RU486 is an abortifacient, these systems are not likely to be useful for developmental studies. Furthermore, the utility of these approaches for long-term protocols is a concern as the response to RU486 diminishes over time. Experiments with these systems have also hinted at the possibility that these chimeric proteins may interfere with endogenous factors, an observation that would explain why it was difficult to generate transgenics that express these proteins. In spite of these issues, an important advantage of steroid-based systems is that they appear to have more favorable kinetics than tetracycline systems, i.e., lipophilic hormones employed by steroid-based systems are quickly metabolized and have short half-lives in vivo.

Accordingly, there remains a need in the art for improved methods to precisely modulate the expression of exogenous genes in mammalian subjects, as well as expanding the range of formulations which can be used to modulate such systems.

BRIEF DESCRIPTION OF THE INVENTION

In accordance with the present invention, there are provided various methods and formulations useful for modulating the expression of exogenous gene(s) in mammalian subject(s). Invention methods and formulations are useful in a wide variety of applications where inducible in vivo expression of exogenous gene(s) is desired, such as in vivo therapeutic methods for delivering recombinant proteins into a variety of cells within a patient.

Unlike prior art tetracycline based strategies, transferring ecdysone responsiveness to mammalian cells takes advantage of a naturally evolved steroid inducible system. Advantages of ecdysteroid use include the lipophilic nature of the compounds (which provides efficient penetration thereof into all tissues, including the brain), short half-lives (which allow for precise and potent inductions), and favorable pharmacokinetics that prevent storage and expedite clearance.

BRIEF DESCRIPTION OF THE FIGURES

In FIG. 1A, the numerical values on both sides of the figure are on different scales, with the left half presenting activity in 10 unit increments and the right half presenting reporter activity in 1000 unit increments. Darkened and stripped bars represent reporter activity with no hormone or 1 $\mu$M muristerone A (MurA), respectively.

FIG. 1B shows FXR and VpEcR activity on ecdysone response element (EcRE) and a hybrid ecdysone/glucocorticoid response element (E/GRE) responsive reporters. VpEcR, VgEcR, and control transfection without receptors were treated with 1 $\mu$M muristerone. FXR transfections were treated with 50 $\mu$M Juvenile Hormone III (Sigma). Darkened and stripped bars represent reporter activity with no hormone or 1 $\mu$M muristerone A/50 $\mu$M Juvenile Hormone III, respectively.

FIG. 1C shows that E/GRE and GRE are non-overlapping response elements. Darkened and stripped bars represent reporter activity with no hormone or 1 $\mu$M muristerone A/1 $\mu$M dexamethasone, respectively.

FIG. 1D shows a schematic diagram of modified ecdysone receptors. GEcR is a chimeric receptor containing the N-terminal transactivation domain of GR and the DNA- and ligand-binding domains of EcR. VpEcR is an N-terminal truncation of EcR fused to the activation domain of Vp16. VgEcR is identical to VpEcR except for the following point mutations in the P box of the DNA binding domain: E282G, G283S, and G286V. Vp16-EcR-B1 is a fusion of full length EcR with the activation domain of Vp16, wherein the activation domain of Vp16 is fused thereto at the carboxy terminus thereof. VgEcR-B1 is identical to Vp16-EcR-B1 except for the same point mutations in the P box of the DNA binding domain as described above. In FIG. 1D, DBD=DNA binding domain and LBD=ligand binding domain.

The ecdysone response elements are placed upstream of a minimal promoter (i.e., an enhancerless promoter) which can drive the expression of any exogenous cDNA.

Figure 3:
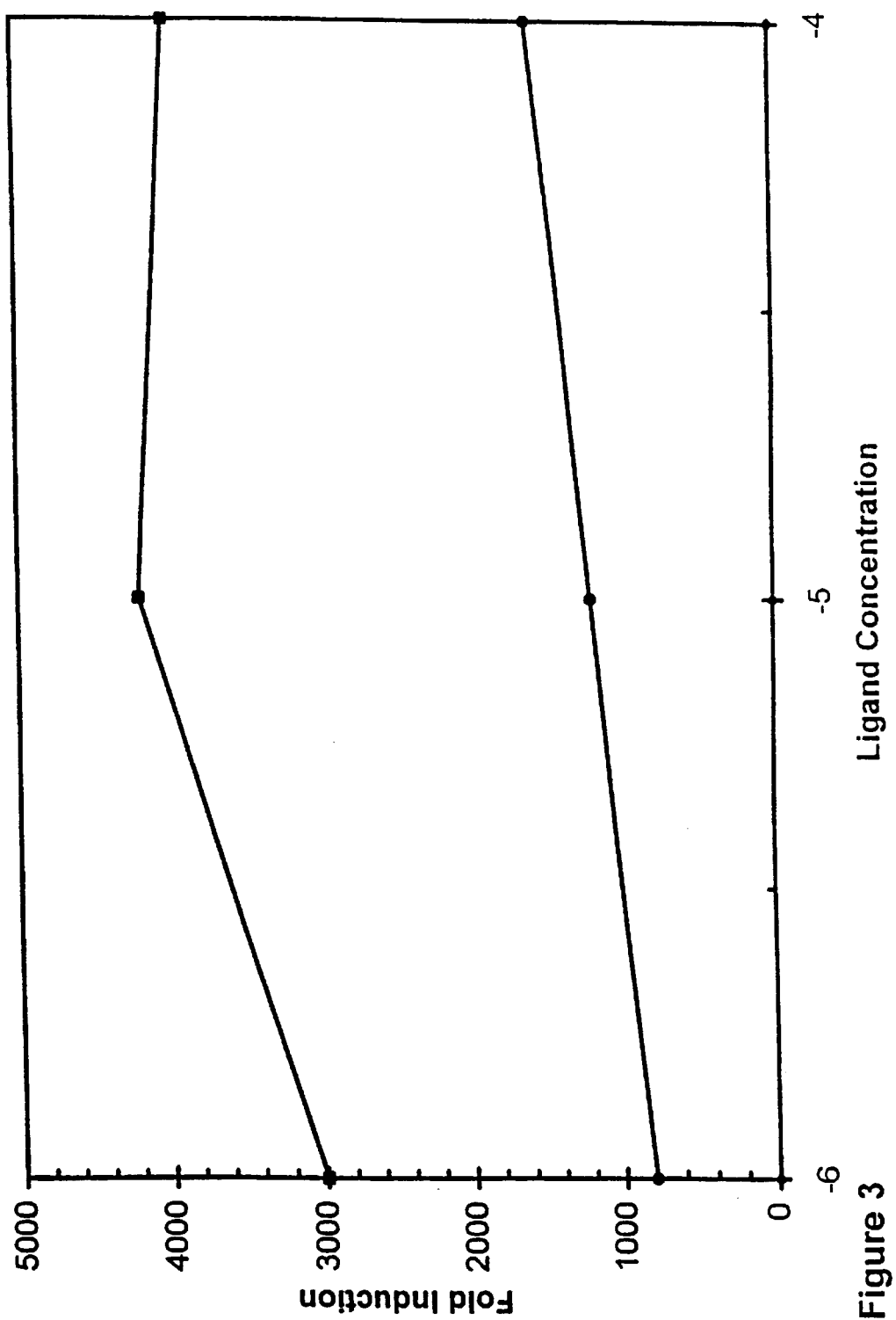

FIG. 3 shows the dose-dependent activation of CV-1 cells with muristerone A alone (●), an RXR ligand (6-(1-(3,5,5, 8,8-pentamethyl-5,6,7,8-tetrahydronaphthalen-2-yl) cyclopropyl)nicotinic acid (LG1000268)) alone (♦), or a combination of the two (MurA and LG1000268; ■), where the concentration of MurA is varied while the concentration of LG1000268 is maintained constant (100 nM).

Figure 4:
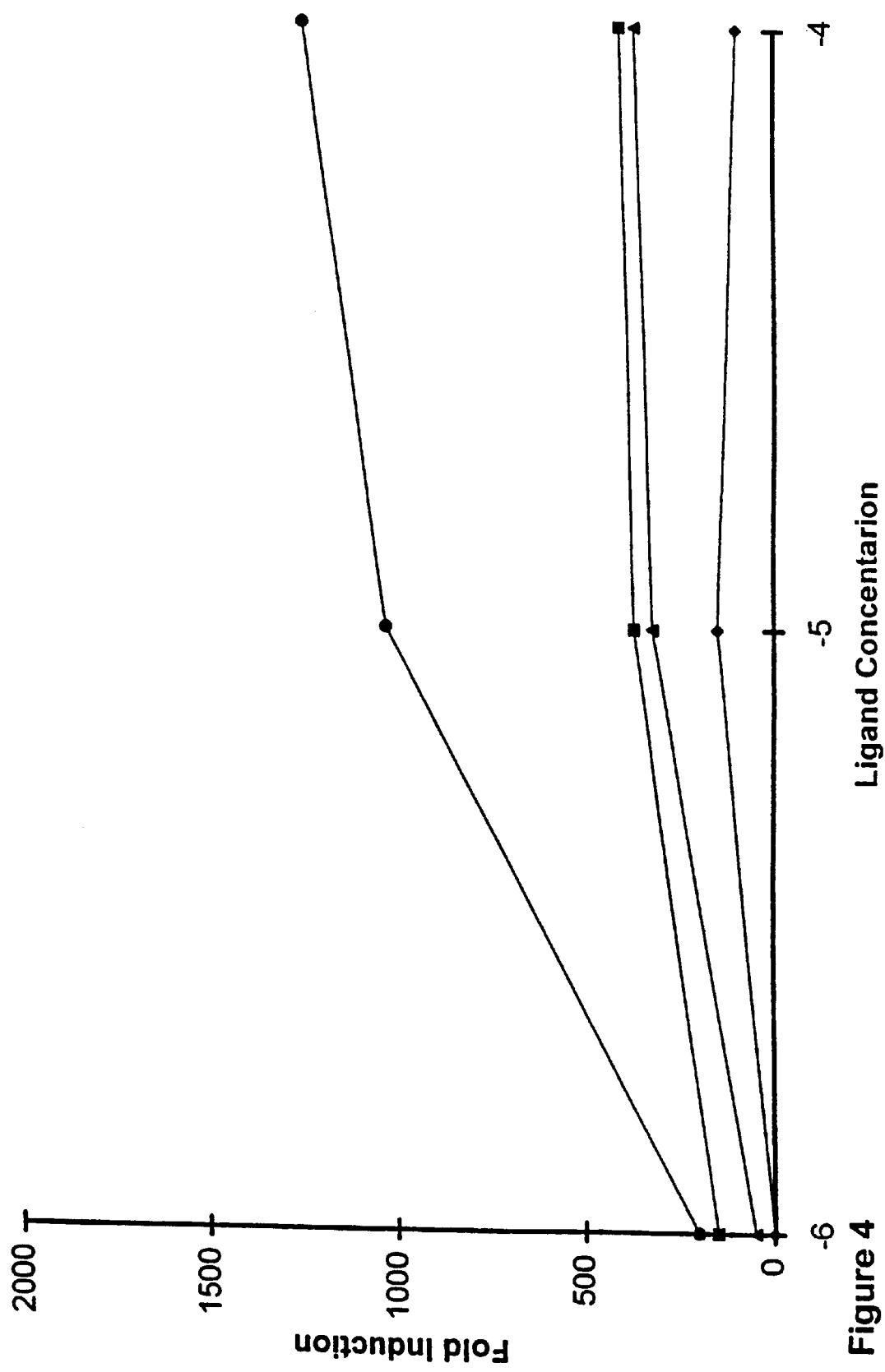

FIG. 4 shows the dose-dependent activation of CV-1 cells with N'-(3,5-dimethylbenzoyl)-N-(2-methyl-3,4-(ethylenedioxy)-benzoyl)-N'-(tert-butyl)hydrazine alone (●) or in the further presence of (6-(1-(3,5,5,8,8-pentamethyl-5,6,7,8-tetrahydronaphthalen-2-yl) cyclopropyl)nicotinic acid (LG1000268), ■), N'-(3,5-dimethylbenzoyl)-N-(4-ethylbenzoyl)-N'-(tert-butyl) hydrazine alone (▲) or in the further presence of LG1000268 (♦).

Figure 5:
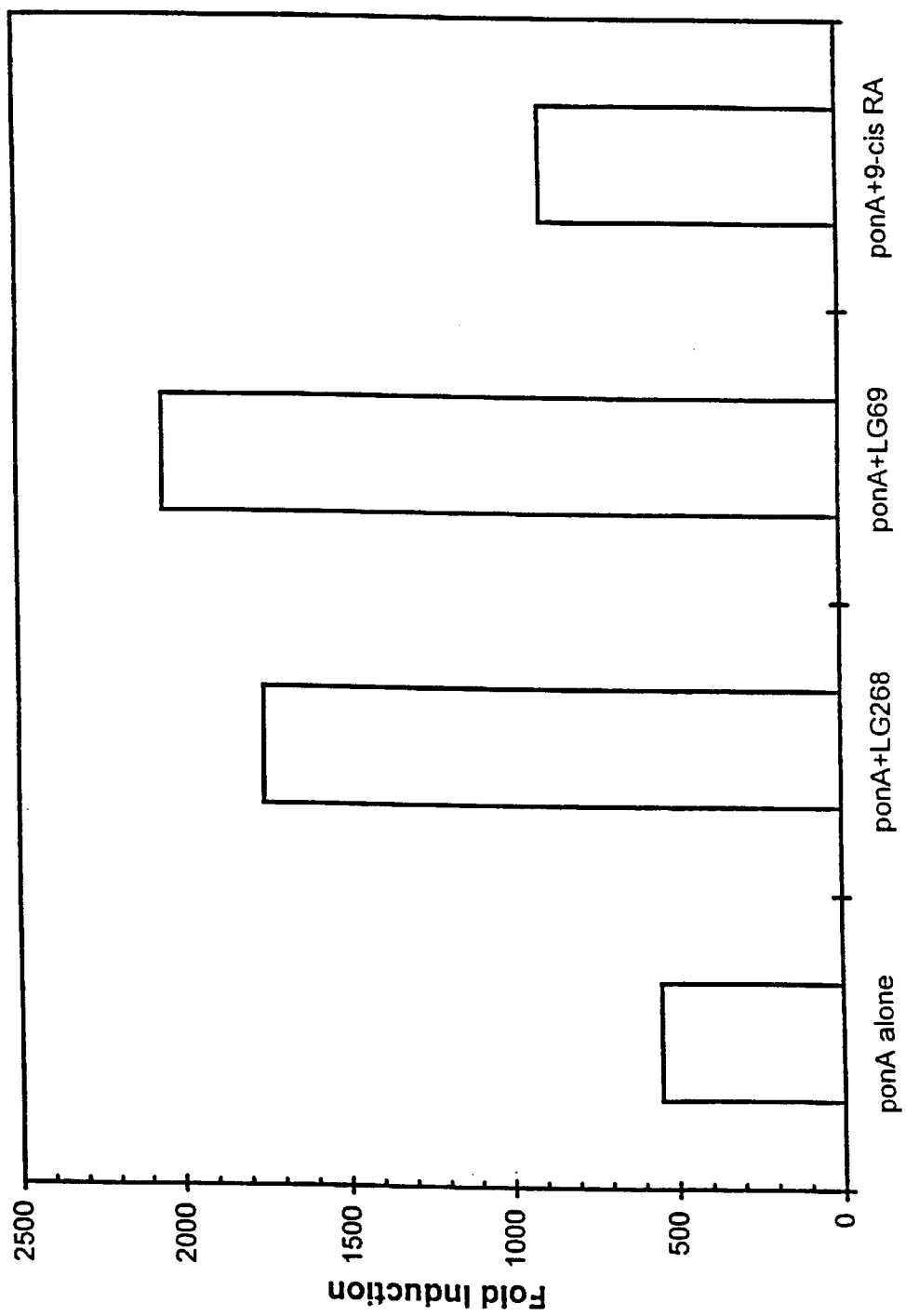

FIG. 5 shows the dose-dependent activation of CV-1 cells with ponasterone A (pona) alone, or in combination with the RXR agonists, LG1000268 ((6-(1-(3,5,5,8,8-pentamethyl-5,6,7,8-tetrahydronaphthalen-2-yl)cyclopropyl)nicotinic acid), LGD1069 (4-(1-(3,5,5,8,8-pentamethyl-5,6,7,8-tetrahydro-2-naphthyl)-ethenyl)benzoic acid) and 9-cis-RA (9-cis-retinoic acid).

DETAILED DESCRIPTION OF THE INVENTION

In accordance with the present invention, there are provided methods for modulating the expression of an exogenous gene in a mammalian subject containing:

(i) a DNA construct comprising said exogenous gene operatively associated with a response element; and (ii) a modified ecdysone receptor which, in the optional presence of a silent partner therefor, is capable of binding to said response element;

said method comprising administering to said subject an effective amount of a first ligand and a second ligand, wherein said first ligand is:

a ligand for said modified ecdysone receptor, not normally present in the cells of said subject, and not toxic to said subject; and wherein said second ligand is a ligand for said silent partner.

Thus, in accordance with the present invention the insect molting hormone, ecdysone (as well as analogs and mimics thereof), is advantageously employed as a regulatable inducer of gene expression in mammalian systems, i.e., background levels of expression are substantially zero in the absence of conditions required for induction. In a presently preferred aspect of the invention, promoters operatively associated with novel modified ecdysone response element (s) are employed in conjunction with modified ecdysone receptor(s) (preferably having altered DNA binding specificity) to provide an extremely powerful and specific inducible mammalian expression system. The low basal activity of the invention expression system is advantageously suitable for the expression of transcription factors and toxic genes. The excellent dose response and induction rate characteristics of the invention inducible expression system allow for precise control of both the degree and duration of induction of a desired gene.

Since the invention method provides for regulated gene expression by an exogenous non-mammalian inducer, it can be advantageously employed in a variety of in vivo, ex vivo and in vitro mammalian expression systems. For example, inducible expression of flp recombinase in transgenic mammals, in accordance with invention methods, would enable those of skill in the art to accomplish temporally specific inducible gene targeting of the adult or the developing embryo (See, e.g., U.S. Pat. Nos. 5,654,182 and 5,677,177).

As employed herein, the terms "modulate" and "modulating" refer to the ability of a given ligand/receptor complex to effect transactivation of transcription of an exogenous gene, relative to such ability of said receptor in the absence of ligand. The actual effect of complex formation on the transactivation activity of a receptor will vary depending on the specific receptor species which are part of the ligand/receptor complex, and on the response element with which the ligand/receptor complex interacts.

As used herein, when referring to genes, the phrase "exogenous to said mammalian subject" or simply "exogenous" refers to any gene wherein the gene product is not naturally expressed in the particular cell where expression is desired. For example, exogenous genes can be either natural, i.e., wild type, or synthetic genes and therapeutic genes, which are introduced into the subject in the form of DNA or RNA. The gene of interest can be introduced into target cells (for in vitro applications), or the gene of interest can be introduced directly into a subject, or indirectly introduced by the transfer of transformed cells into a subject. When referring to ligands, inducers or activators, the term "exogenous" refers to compounds which originate or are produced outside the particular cell or organism where expression is desired.

"Wild type" genes are those that are native to cells of a particular type. Wild type genes contemplated for use in the practice of the present invention include genes which encode a gene product:

the substantial absence of which leads to the occurrence of a non-normal state in said subject; or a substantial excess of which leads to the occurrence of a non-normal state in said subject;

and the like.

Such genes may not be expressed in biologically significant levels or may be undesirably overexpressed, respectively, to result in a non-normal state, such as diseases, injuries, maladies, neoplasms, disorders, infections, and the like. Thus, for example, while a synthetic or natural gene encoding human insulin would be exogenous genetic material to a yeast cell (since yeast cells do not naturally contain insulin genes), a human insulin gene inserted into a human skin fibroblast cell would be a wild type gene with respect to the fibroblast since human skin fibroblasts contain genetic material encoding human insulin, although human skin fibroblasts do not express human insulin in biologically significant levels.

As employed herein, the phrase "therapeutic gene" refers to a gene which imparts a beneficial function to the host cell in which such gene is expressed. Therapeutic genes are those that are not naturally found in host cells. For example, a synthetic or natural gene coding for wild type human insulin would be therapeutic when inserted into a skin fibroblast cell so as to be expressed in a human host, where the human host is not otherwise capable of expressing functionally active human insulin in biologically significant levels. In accordance with the methods described herein, therapeutic genes are expressed at a level that provides a therapeutically effective amount of the corresponding therapeutic protein.

Therapeutic genes contemplated for use in the practice of the present invention include genes which encode a gene product:

which is toxic to the cells in which it is expressed; or which imparts a beneficial property to the host subject (e.g., disease resistance, etc);

and the like.

Numerous genomic and cDNA nucleic acid sequences coding for a variety of proteins are well known in the art. Exogenous genetic material useful in the practice of the present invention include genes that encode biologically active proteins of interest, such as, e.g., secretory proteins that can be released from said cell; enzymes that can metabolize a substrate from a toxic substance to a non-toxic substance, or from an inactive substance to a useful substance; regulatory proteins; cell surface receptors; and the like. Useful genes include genes that encode blood clotting factors such as human factors VIII and IX; genes that encode hormones such as insulin, parathyroid hormone, luteinizing hormone releasing factor (LHRH), alpha and beta seminal inhibins, and human growth hormone; genes that encode proteins such as enzymes, the absence of which leads to the occurrence of an abnormal state; genes encoding cytokines or lymphokines such as interferons, granulocytic macrophage colony stimulating factor (GM-CSF), colony stimulating factor-1 (CSF-1), tumor necrosis factor (TNF), and erythropoietin (EPO); genes encoding inhibitor substances such as $alpha_1$-antitrypsin; genes encoding substances that function as drugs, e.g., genes encoding the diphtheria and cholera toxins; and the like.

Typically, nucleic acid sequence information for a desired protein can be located in one of many public access databases, e.g., GENBANK, EMBL, Swiss-Prot, and PIR, or in many biology related journal publications. Thus, those of skill in the art have access to nucleic acid sequence information for virtually all known genes. Those of skill in the art can either obtain the corresponding nucleic acid molecule directly from a public depository or the institution that published the sequence. Optionally, once the nucleic acid sequence encoding a desired protein has been ascertained, the skilled artisan can employ routine methods, e.g., polymerase chain reaction (PCR) amplification, to isolate the desired nucleic acid molecule from the appropriate nucleic acid library. Thus, all known nucleic acids encoding proteins of interest are available for use in the methods and products described herein.

As used herein, the terms "mammal" and "mammalian" refer to humans; domesticated animals, e.g., rats, mice, rabbits, canines, felines, and the like; farm animals, e.g., chickens, cows, pigs and sheep, and the like; and animals of zoological interest, e.g., monkeys and baboons, and the like.

Modified ecdysone receptors contemplated for use in the practice of the present invention comprise:

a ligand binding domain capable of binding an ecdysteroid;

a DNA-binding domain, preferably obtained from a DNA-binding protein; and an activation domain, preferably of a transcription factor, wherein at least one of said DNA-binding domain or said activation domain is not obtained from a native ecdysone receptor.

Preferably, when said activation domain is derived from a glucocorticoid receptor, said DNA-binding domain is not derived from a glucocorticoid receptor or an *E. coli* LexA protein. In accordance with the present invention, modified ecdysone receptors function in expression systems, preferably mammalian, to transactivate gene expression from transcription regulatory regions having ecdysone response elements. Preferably, in order to minimize induction of undesired gene expression, modified ecdysone receptors of the invention will have substantially no constitutive activity in mammalian cells.

Ligand binding domains capable of binding an ecdysteroid, as contemplated for use in the preparation of invention modified ecdysone receptors are typically derived from the carboxy-terminal portion of native ecdysone receptor (see, for example, Koelle et al., *Cell,* 67:59–77, 1991; Christopherson et al., *PNAS, USA,* 89:6314–6318, 1992; Jepson et al. WO 96/37609, 1996). Ligand binding domains capable of binding an ecdysteroid can be functionally located in either orientation and at various positions within the modified ecdysone receptor of the invention. For example, the ligand binding domain capable of binding an ecdysteroid can be positioned at either the amino or carboxy terminus of the modified receptor, or therebetween. In a preferred embodiment of the present invention, the ligand binding domain capable of binding an ecdysteroid is positioned at the carboxy terminus of the modified receptor (see FIG. 1).

DNA-binding domains contemplated for use in the preparation of modified ecdysone receptors contemplated for use in the practice of the present invention are typically obtained from DNA-binding proteins (e.g., transcription factors). The term "DNA-binding domain" is understood in the art to refer to an amino acid sequence that is able to bind to DNA. As used herein, the term "DNA-binding domain" encompasses a minimal peptide sequence of a DNA-binding protein, up to the entire length of a DNA-binding protein, so long as the DNA-binding domain functions to associate with a particular response element.

Such DNA-binding domains are known to function heterologously in combination with other functional protein domains by maintaining the ability to bind the natural DNA recognition sequence (see, e.g., Brent and Ptashne, 1985, *Cell,* 43:729–736). For example, hormone receptors are known to have interchangeable DNA-binding domains that function in chimeric proteins (see, e.g., U.S. Pat. No. 4,981, 784; and Evans, R., 1988, *Science,* 240:889–895). Thus, similar to the ligand binding domain of invention modified ecdysone receptor, the DNA-binding domain can be positioned at either the carboxy terminus or the amino terminus, or the DNA-binding domain can be positioned between the ligand binding domain and the activation domain. In preferred embodiments of the present invention, the DNA-binding domain is positioned internally between the ligand binding domain and the activation domain.

"DNA-binding protein(s)" contemplated for use herein belong to the well-known class of proteins that are able to directly bind DNA and facilitate initiation or repression of transcription. Exemplary DNA-binding proteins contemplated for use herein include transcription control proteins (e.g., transcription factors and the like; Conaway and Conaway, 1994, "Transcription Mechanisms and Regulation", *Raven Press Series on Molecular and Cellular Biology,* Vol. 3, Raven Press, Ltd., New York, N.Y.).

Transcription factors contemplated for use herein as a source of such DNA binding domains include, e.g., homeobox proteins, zinc finger proteins, hormone receptors, helix-turn-helix proteins, helix-loop-helix proteins, basic-Zip proteins (bZip), β-ribbon factors, and the like. See, for example, Harrison, S., "A Structural Taxonomy of DNA-binding Domains," *Nature,* 353:715–719. Homeobox DNA-binding proteins suitable for use herein include, for example, HOX, STF-1 (Leonard et al., 1993, *Mol. Endo.*, 7:1275–1283), Antp, Mat α-2, INV, and the like. See, also, Scott et al. (1989), *Biochem. Biophys. Acta,* 989:25–48. It has been found that a fragment of 76 amino acids (corresponding to amino acids 140–215 described in Leonard et al., 1993, *Mol. Endo.,* 7:1275–1283) containing the STF-1 homeodomain binds DNA as tightly as wild-type STF-1. Suitable zinc finger DNA-binding proteins for use herein include Zif268, GLI, XFin, and the like. See also, Klug and Rhodes (1987), *Trends Biochem. Sci.,* 12:464; Jacobs and Michaels (1990), *New Biol.,* 2:583; and Jacobs (1992), *EMBO J.,* 11:4507–4517.

An additional DNA binding domain contemplated for use in the practice of the present invention is the GAL4 DNA binding domain. The DNA binding domain of the yeast GAL4 protein comprises at least the first 74 amino terminal amino acids thereof (see, for example, Keegan et al., *Science* 231:699–704 (1986)). Preferably, the first 90 or more amino terminal amino acids of the GAL4 protein will be used, with the 147 amino terminal amino acid residues of yeast GAL4 being presently most preferred.

Preferably, the DNA-binding domain used herein is obtained from a member of the steroid/thyroid hormone superfamily of receptors. As used herein, the phrase "member(s) of the steroid/thyroid hormone superfamily of receptors" (also known as "nuclear receptors" or "intracellular receptors") refers to hormone binding proteins that operate as ligand-dependent transcription factors, including identified members of the steroid/thyroid hormone superfamily of receptors for which specific ligands have not yet been identified (referred to hereinafter as "orphan receptors").

Exemplary members of the steroid/thyroid hormone superfamily of receptors (including the various isoforms thereof) include steroid receptors such as glucocorticoid receptor (GR), mineralocorticoid receptor (MR), estrogen receptor (ER), progesterone receptor (PR), androgen receptor (AR), vitamin $D_3$ receptor (VDR), various isoforms of peroxisome proliferator-activated receptors (PPARs), and the like; plus retinoid receptors, such as the various isoforms of retinoic acid receptor (e.g., RARα, RARβ, or RARγ), the various isoforms of retinoid X receptor (e.g., RXRα, RXRβ, or RXRγ), and the like (see, e.g., U.S. Pat. Nos. 4,981,784; 5,171,671; and 5,071,773); thyroid receptors (TR), such as TRα, TRβ, and the like; insect derived receptors such as the ecdysone receptor, and the like; as well as other gene products which, by their structure and properties, are considered to be members of the superfamily, as defined hereinabove, including the various isoforms thereof. Examples of orphan receptors contemplated for use herein as a source of DNA binding domain include HNF4 (see, for example, Sladek et al., in *Genes & Development* 4: 2353–2365 (1990)), the COUP family of receptors (see, for example, Miyajima et al., in *Nucleic Acids Research* 16: 11057–11074 (1988), and Wang et al., in *Nature* 340: 163–166 (1989)), COUP-like receptors and COUP homologs, such as those described by Mlodzik et al., in *Cell* 60: 211–224 (1990) and Ladias et al., in *Science* 251: 561–565 (1991), the insect derived knirps and knirps-related receptors, and the like.

The DNA-binding domains of all members of the steroid/thyroid hormone superfamily of receptors are related, consisting of 66–68 amino acid residues, and possessing about 20 invariant amino acid residues, including nine cysteines. A member of the superfamily can be characterized as a protein which contains these 20 invariant amino acid residues. The highly conserved amino acids of the DNA-binding domain of members of the superfamily are as follows:

Cys-X-X-Cys-X-X-Asp*-X-Ala*-X-Gly*-X-Tyr*-X-X-X-X-Cys-X-X-Cys-Lys*-X-Phe-Phe-X-Arg*-X-X-X-X-X-X-X-X-(X-X-)Cys-X-X-X-X-X-X-(X-X-X-)Cys-X-X-X-Lys-X-X-Arg-X-X-Cys-X-X-Cys-Arg*-X-X-Lys*-Cys-X-X-X-Gly*-Met (SEQ ID NO:1);

wherein X designates non-conserved amino acids within the DNA-binding domain; an asterisk denotes the amino acid residues which are almost universally conserved, but for which variations have been found in some identified hormone receptors; and the residues enclosed in parenthesis are optional residues (thus, the DNA-binding domain is a minimum of 66 amino acids in length, but can contain several additional residues).

Modification of existing DNA-binding domains to recognize new and/or specific target recognition sequences is also contemplated herein. For example, in accordance with the present invention, it has been found that the modification of the "P-box" sequence of DNA-binding domains of members of the steroid/thyroid hormone superfamily of receptors offers unique advantages not present in other chimeric hormone receptors. For example, the modification of a P-box amino acid sequence to preferentially bind to a different hormone response element half-site than the naturally occurring P-box amino acid sequence can reduce undesired background levels of gene expression. Thus, invention receptors and methods provide the advantage of increasing the selectivity of exogenous gene expression in a particular subject.

Figure 2:
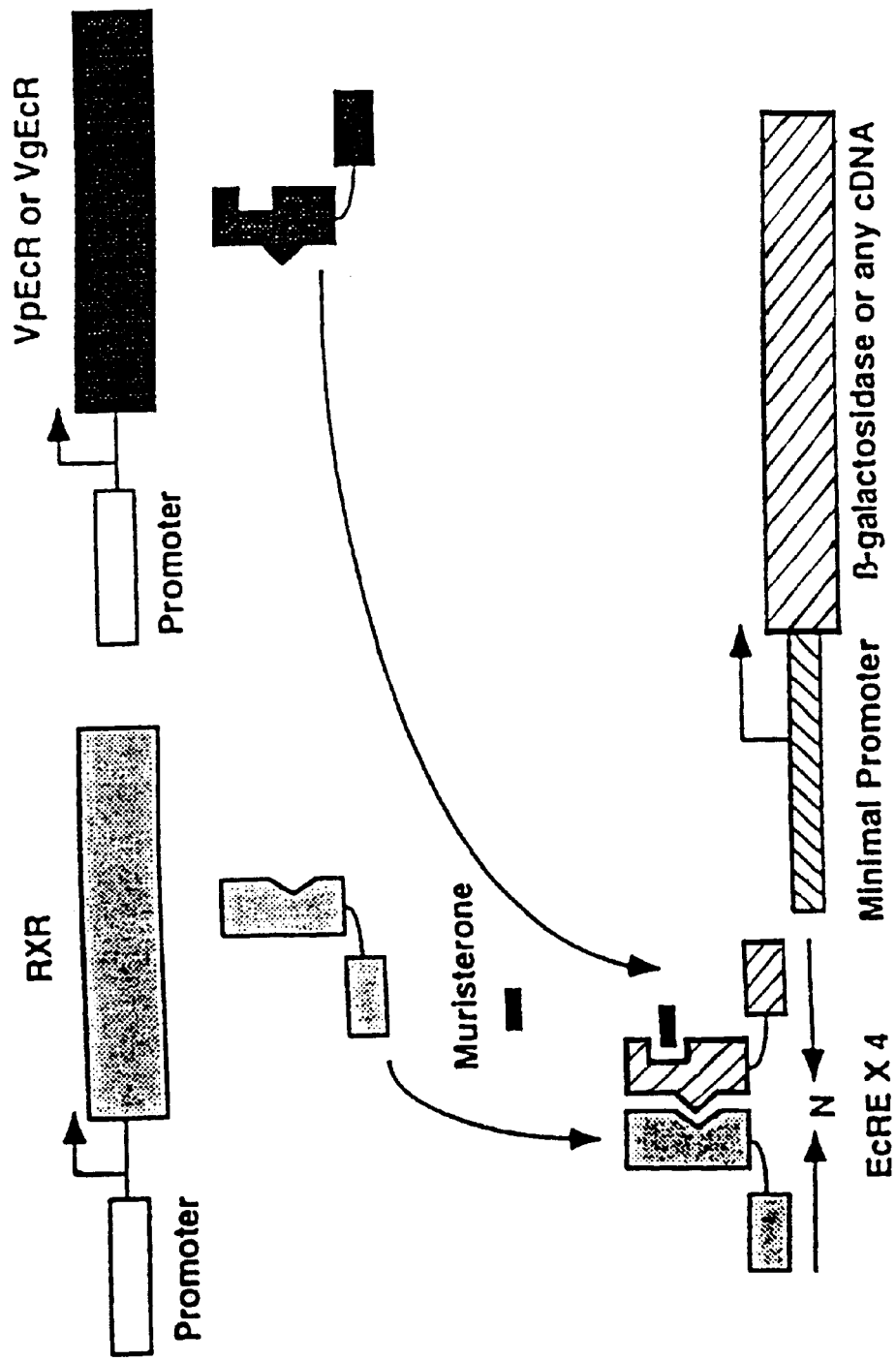
FIG. 2 shows a schematic diagram of an invention ecdysone inducible gene expression system. After expression of RXR and a modified EcR, the two receptors can heterodimerize and transactivate the ecdysone response element-containing promoter in the presence of hormone.

As used herein, the phrase "P-box amino acid sequence" refers to the proximal element region in a DNA-binding domain of a hormone receptor that typically occurs at the junction of the first zinc finger and the linker region, e.g., at about amino acids 19–23 of the DNA-binding domain (i.e., amino acids 19–23 of SEQ ID NO:1; see, e.g., Umesono et al. (1989), *Cell,* 57;1139–1146, FIG. 2). Umesono et al. (1989), supra, in Table 1, describe various naturally occurring P-box amino acid sequences for a variety of hormone receptor DNA-binding domains.

In one embodiment of the present invention, the P-box sequence of a hormone receptor DNA-binding domain is modified to have a P-box amino acid sequence that differs from the naturally occurring P-box amino acid sequence. In a preferred embodiment of the present invention, the modified P-box amino acid sequence differs from the naturally occurring P-box amino acid sequence by 3 amino acids.

Preferably, the P-box amino acid sequence is modified so that only the half-site nucleotide sequence recognized by the DNA-binding domain is changed while not altering the spacing between the two half-sites recognized by the DNA-binding domain. For example, when the DNA-binding domain of the ecdysone receptor is employed in an invention modified ecdysone receptor, the P-box can be modified from the amino acid sequence EGCKG (SEQ ID NO:2; which recognizes the half-site -AGGTCA-) to the amino acid sequence GSCKV (SEQ ID NO:3; which recognizes the half-site seqence -AGAACA-). In a presently preferred embodiment, when the DNA-binding domain of invention modified ecdysone receptor is derived from ecdysone receptor, the P-box amino acid sequence is modified to GSCKV (SEQ ID NO:3).

It has also been found that in vitro evolution methods can be applied to modify and improve existing DNA-binding domains (see, e.g., Devlin et al., 1990, *Science,* 249:404–406; and Scott and Smith, 1990, *Science,* 249:386–390). Alternatively, DNA-binding domains which are engineered with novel DNA-recognition specificity (see, e.g., Pomerantz et al. Science 267:93–96, 1995, ZFHD1, an engineered transcription factor with a composite DNA-binding domain) are also contemplated.

Activation domains contemplated for use in the preparation of invention modified ecdysone receptor are typically derived from transcription factors and comprise a contiguous sequence of amino acids that functions to activate gene expression when associated with a suitable DNA-binding domain and a suitable ligand binding domain. As with the ligand and DNA-binding domains employed for the preparation of invention modified ecdysone receptors, the activation domain can be positioned at the carboxy terminus, the amino terminus or between the ligand binding domain and the DNA binding domain. In preferred embodiments of present invention, the activation domain is positioned at the amino terminus of the modified ecdysone receptor.

Suitable activation domains can be obtained from a variety of sources, e.g., from the N-terminal region of a member of the steroid/thyroid hormone superfamily of receptors, from a transcription factor activation domain, such as, for example, VP16, GAL4, NF-κB or BP64 activation domains, and the like. The presently most preferred activation domain contemplated for use in the practice of the present invention is obtained from the N-terminal region of the VP16 protein.

The presently most preferred modified ecdysone receptors contemplated for use herein are VgEcR, VpEcR, GEcR, Vp16-EcR-B1 or VgEcR-B1 (see FIG. 1). VgEcR, VgEcR-B1, and Vp16-EcR-B1 are the presently most preferred receptors contemplated for use herein. The preparation of several of these modified ecdysone receptors is set forth hereinafter in Example 1. Those modified receptors for which explicit methods of preparation is not provided herein can readily be made using the methodology set forth herein in combination with standard methodology well known to those of skill in the art.

Invention modified ecdysone receptor proteins can be produced by expressing nucleic acid constructs encoding the chimeric proteins in suitable host cells as described in Example 1. Recombinant methods of producing desired proteins by introducing an expression construct into appropriate host cells are well-known in the art. Modified ecdysone receptors of the invention can be introduced into a particular subject by direct introduction of the proteins themselves, by introducing DNA construct(s) encoding the receptor into the subject, or into cells obtained from the subject (wherein the cells are transformed and subsequently returned to the subject).

In a preferred embodiment, invention modified ecdysone receptors are expressed under the control of a tissue specific promoter. As readily understood by those of skill in the art, the term "tissue specific" refers to the substantially exclusive initiation of transcription in the tissue from which a particular promoter drives expression of a given gene.

In accordance with one aspect of the present invention, invention modified ecdysone receptors are present in the form of heterodimeric species comprising an invention modified ecdysone receptor and at least one silent partner of the steroid/thyroid hormone superfamily of receptors. Preferably, the silent partner is a mammalian-derived receptor, with RXR being especially preferred.

Silent partners contemplated herein are members of the steroid thyroid hormone superfamily of receptors which are capable of forming heterodimeric species with the invention modified ecdysone receptor, wherein the silent partner does not directly participate in binding the first ligand (i.e., the ecdysteroid receptor binds the first ligand) but enhances or synergizes ecdysteroid receptor transcription activity upon association with the second ligand. The silent partner can either be endogenous to the cells of the subject or can be provided to the subject by introducing DNA construct(s) encoding receptor into the subject. A preferred silent partner for use herein is RXR. In a particular embodiment of the present invention, exogenous RXR is provided to said mammalian subject in conjunction with or independent of the invention modified ecdysone receptor.

The formation of heterodimeric receptor(s) can modulate the ability of member(s) of the steroid/thyroid hormone superfamily of receptors to trans-activate transcription of genes maintained under expression control in the presence of ligand for the receptor. For example, formation of a heterodimer of the modified ecdysone receptor with another mammalian hormone receptor promotes the ability of the modified ecdysone receptor to induce trans-activation activity in the presence of an ecdysone response element.

In accordance with another aspect of the present invention, invention modified ecdysone receptors are present in the form of homodimeric species comprising a plurality (i.e., at least two) of invention modified ecdysone receptors, wherein the homodimeric species is capable of associating with RXR, preferably endogenous RXR.

Ligands contemplated for use herein (i.e., the "first" and "second" ligand referred to herein) are compounds which, inside a cell, interact (directly or indirectly) with a homodimer or heterodimer including invention modified ecdysone receptor(s) and silent partner therefor, thereby creating a ligand/receptor complex, which in turn can induce transcription through an appropriate response element. The terms "ecdysone", "ecdysteroid", "ecdysone-analogs", and "ecdysone mimics" as interchangeably used herein, are employed herein in the generic sense (in accordance with common usage in the art), referring to a family of ligands (i.e., first ligand (also referred herein as "activator," "agonist" or "inducer") with the appropriate transactivation activity (see, for example, Cherbas et al., in *Biosynthesis, metabolism and mode of action of invertebrate hormones* (ed. J. Hoffmann and M. Porchet), p. 305–322; Springer-Verlag, Berlin). An ecdysone, therefore, is a steroid, steroid-like or non-steroidal compound which acts to modulate gene transcription for a gene maintained under the control of a suitable response element, as described herein.

20-Hydroxy-ecdysone (also known as β-ecdysone) is the major naturally occurring ecdysone. Unsubstituted ecdysone (also known as α-ecdysone) is converted in peripheral tissues to β-ecdysone. Analogs of the naturally occurring ecdysones are also contemplated within the scope of the present invention. Examples of such analogs, commonly referred to as ecdysteroids, include ponasterone A, ponasterone B, ponasterone C, ponasterone D, 26-iodoponasterone A, muristerone A, inokosterone, 26-mesylinokosterone, sidasterone, buterosterone, ajugasterone, makisterone, cyasterone, sengosterone, and the like. Since it has been previously reported that the above-described ecdysones are neither toxic, teratogenic, nor known to affect mammalian physiology, they are ideal candidates for use as inducers in cultured cells and transgenic mammals according to the invention methods.

Additional compounds contemplated for use herein are mimics of the naturally occurring ecdysones, i.e., synthetic organic compounds which have transactivation activity characteristic of the naturally occurring ecdysones. Examples of such compounds, referred to herein as ecdysone mimics, include 1,2-diacyl hydrazines (e.g., those described in U.S. Pat. Nos. 5,424,333 and 5,354,762, the entire contents of each of which are hereby incorporated by reference herein), N'-substituted-N,N'-di-substituted hydrazines (e.g., those described in U.S. Pat. No. 5,117,057, the entire contents of which are hereby incorporated by reference herein), dibenzoylalkyl cyanohydrazines (e.g., those described in European Application No. 461,809, the entire contents of which are hereby incorporated by reference herein), N-substituted-N-alkyl-N,N'-diaroyl hydrazines (e.g., those described in U.S. Pat. No. 5,225,443, the entire contents of which are hereby incorporated by reference herein), N-substituted-N-acyl-N-alkyl, carbonyl hydrazines (e.g., those described in European Application No. 234,944, the entire contents of which are hereby incorporated by reference herein), N-aroyl-N'-alkyl-N'-aroyl hydrazines (e.g., those described in U.S. Pat. No. 4,985,461, the entire contents of which are hereby incorporated by reference herein), and the like. Compounds of specific interest are those having the formula:

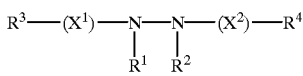

wherein:

$R^1$ is optionally hydrogen, lower alkyl or substituted lower alkyl, alkenyl or substituted alkenyl, alkynyl or substituted alkynyl, aryl or substituted aryl, heteroaryl or substituted heteroaryl, and the like. $R^1$ is not present when $X^1$ is part of a carbon-nitrogen double bond linking $R^3$ to the hydrazino group.

$R^2$ is optionally hydrogen, alkyl or substituted alkyl, cyclohexyl or substituted cyclohexyl, and the like. $R^2$ is not present when $X^2$ is part of a carbon-nitrogen double bond linking $R^4$ to the hydrazino group.

$R^3$ and $R^4$ are independently part of an appropriately substituted carbon-nitrogen double bond which links $R^3$ and/or $R^4$ to the hydrazino linkage, or $R^3$ and $R^4$ are independently aryl or substituted aryl, heteroaryl or substituted heteroaryl, provided, however, that when two adjacent positions on the aryl or heteroaryl moieties are substituted with alkoxy, thioalkyl, alkylamino, or dialkylamino groups, these groups may be joined to form a 5- or 6-membered heterocyclic ring system, or $R^3$ and $R^4$ are independently heterocyclic or substituted heterocyclic, cycloalkyl or substituted cycloalkyl, and the like.

$X^1$ and $X^2$ are independently —C(O)—, —C(S)—, —C(NR$_2$)—, —C(=CN)NH—, —C(O)O—, —C(O)NH—, —C(O)NHSO$_2$—, —CH$_2$—, —SO$_2$—, —P(O)CH$_3$—, and the like, as well as an appropriate substituted carbon-nitrogen double bond which links $R^3$ and/or $R^4$ to the hydrazino linkage.

As employed herein, "alkyl" refers to alkyl groups having in the range of 1 up to 8 carbon atoms; "lower alkyl" refers to alkyl groups having in the range of 1 up to 4 carbon atoms; and "substituted alkyl" or "substituted lower alkyl" comprises alkyl (or lower alkyl) groups further bearing one or more substituents selected from halogen, cyano, nitro, hydroxy, alkoxy (—OR), thioalkyl (—SR), —NR$_2$, —NRC(O)R, —OC(O)R, —C(O)OR, —C(O)NR$_2$, —C(O)R, wherein each R is independently hydrogen or lower alkyl, and the like.

As employed herein, "cycloalkyl" refers to cyclic ring-containing groups containing in the range of about 5 up to 8 carbon atoms, and "substituted cycloalkyl" refers to cycloalkyl groups further bearing one or more substituents as set forth above, as well as lower alkyl.

As employed herein, "heterocyclic" refers to cyclic (i.e., ring-containing) groups containing one or more (up to four) heteroatoms (e.g., N, O, S, or the like) as part of the ring structure, and having in the range of 2 up to 5 nuclear carbon atoms and "substituted heterocyclic" refers to heterocyclic groups further bearing one or more substituents as set forth above, as well as lower alkyl.

As employed herein, "alkenyl" refers to straight or branched chain hydrocarbyl groups having at least one carbon-carbon double bond, and having in the range of about 2 up to 12 carbon atoms, and "substituted alkenyl" refers to alkenyl groups further bearing one or more substituents as set forth above.

As employed herein, "alkynyl" refers to straight or branched chain hydrocarbyl groups having at least one carbon-carbon triple bond, and having in the range of about 2 up to 12 carbon atoms, and "substituted alkynyl" refers to alkynyl groups further bearing one or more substituents as set forth above.

As employed herein, "aryl" refers to aromatic groups having in the range of 6 up to 14 carbon atoms and "substituted aryl" refers to aryl groups further bearing one or more substituents as set forth above, as well as lower alkyl.

As employed herein, "heteroaryl" refers to aromatic groups containing one or more heteroatoms (e.g., N, O, S, or the like) as part of the ring structure, and having in the range of 3 up to 14 carbon atoms and "substituted heteroaryl" refers to heteroaryl groups further bearing one or more substituents as set forth above.

Presently preferred ecdysone mimics contemplated for use herein include compounds wherein $R^1$ is hydrogen; $R^2$ is an alkyl group possessing considerable bulk (such as, for example, alkyl groups containing a tertiary carbon center, e.g., —C(R")$_3$, wherein each R" is methyl or greater). Examples of alkyl groups having sufficient bulk for use herein include tert-butyl, sec-butyl, isopropyl, isobutyl, cyclohexyl, cyclopentyl, dicyclopropylmethyl, (cyclohexyl) ethyl, and the like); $X^1$ and $X^2$ are both —C(O)—; $R^3$ is phenyl, substituted phenyl (with hydroxy, alkoxy, halo and/or substituted amino substituents being preferred, with 3,4-disubstitution pattern being especially preferred), heterocyclic (e.g., pyridyl or pyrimidine) or substituted heterocyclic (with halo, alkyl, thioalkyl, hydroxy, alkoxy, and/or amino substituents being preferred); and $R^4$ is phenyl or substituted phenyl, heteroaryl or substituted heteroaryl or a bulky alkyl or cycloalkyl group.

Especially preferred ecdysone mimics contemplated for use herein include N'-(3,5-dimethylbenzoyl)-N-(4-ethylbenzoyl)-N'-(tert-butyl)hydrazine, N,N'-dibenzoyl-N'-(tert-butyl) hydrazine, N'-(3,5-dimethylbenzoyl)-N-(4-ethylbenzyl)-N'-(tert-butyl)hydrazine, N'-(3,5-dimethylbenzoyl)-N-(2-methyl-3,4-(ethylenedioxy)-benzoyl)-N'-(tert-butyl)hydrazine, 3,5-di-tert-butyl-4-hydroxy-N-isobutyl-benzamide, 8-O-acetylharpagide, and the like.

Ecdysone or ecdysone-like ligands contemplated for use in the practice of the present invention are characterized as not normally being present in the cells of the subject, meaning that the first ligand is exogenous to the subject. Ecdysteroids, for example, are not naturally present in mammalian systems. Thus, in accordance with the invention method, unless and until an ecdysteroid is administered to the subject, substantially no expression of the desired gene occurs.

As readily recognized by those of skill in the art, it may be desirable to be able to rapidly induce or rapidly turn off expression utilizing the regulatory system of the invention. This can readily be accomplished by administration of a suitable ecdysone antagonist before or after induction of the system (e.g., to prevent undesired activation of the system, to promote rapid induction, to rapidly terminate expression, and the like). Numerous naturally-occurring and synthetic ecdysone antagonists are known in the art, e.g., ajugalactone.

The second ligand contemplated for use in the practice of the present invention is a compound which interact (directly or indirectly) with a silent partner for the modified ecdysone receptor described herein. While such ligands alone impart virtually no activity to the invention expression system, they have been discovered to greatly enhance the ability of ecdysone or ecdysone-like compounds to activate the invention expression system. Those of skill in the art can readily determine suitable ligands for the silent partner being employed. A presently preferred silent partner is RXR; exemplary RXR agonists contemplated for use herein include 9-cis-retinoic acid, 4-(1-(3,5,5,8,8-pentamethyl-5,6,7,8-tetrahydro-2-naphthyl)-ethenyl)benzoic acid (3-methyl-TTNEB; LGD 1069), ((E)-2-(2-((5,6,7,8-tetra-hydro-3,5,5,8,8-pentamethyl-2-naphthyl)propen-1-yl)-4-thiophenecarboxylic acid) (AGN 191701), 2-(5,6,7,8-tetra-hydro-5,5,8,8-tetramethyl-2-naphthyl)-2-(carboxyphenyl)-1,3-dioxolane (SR 11237), 4-(5H-2,3-(2,5-dimethyl-2,5-hemano)-5-methyl-dibenzo(b,e) (1,4)diazepin-11-yl)-benzoic acid (HX600) or thiadiazepin analogs thereof, 3,7,11,15-tetramethyl hexadecanoic acid (phytanic acid), 6-(1-(3,5,5,8,8-pentamethyl-5,6,7,8-tetrahydronaphthalen-2-yl) cyclopropyl)nicotinic acid (LG1000268), 2-(4-carboxyphenyl)-2-(5,6,7,8-tetrahydro-5,5,8,8-tetramethyl-2-naphthalenyl)-1,3-dithiane (SR11203), 4-(2-methyl)-1-(5,6,7,8-tetrahydro-5,5,8,8-tetramethyl-2-naphthalenyl) propenyl)benzoic acid (SR11217), and the like.

An effective amount of each of first and second ligand contemplated for use in the practice of the present invention is the amount of each ligand required to achieve the desired level of gene expression product. Ligand(s) can be administered in a variety of ways, as are well-known in the art. For example, such ligands can be administered topically, orally, intravenously, intraperitoneally, intravascularly, and the like. The first and second ligand can be administered concurrently or independently.

In accordance with a particular embodiment of the present invention, pharmaceutically acceptable formulations, and kits thereof, comprising at least one activator for a modified ecdysone receptor as described herein, at least one ligand for a silent partner for the modified ecdysone receptor, and a pharmaceutically acceptable carrier are contemplated. In accordance with another aspect of the present invention, pharmaceutically acceptable formulations consisting essentially of at least one activator for a modified ecdysone receptor as described herein, at least one ligand for a silent partner for the modified ecdysone receptor, and a pharmaceutically acceptable carrier, are contemplated. Pharmaceutical formulations of the present invention can be used in the form of a solid, a solution, an emulsion, a dispersion, a micelle, a liposome, and the like, wherein the resulting formulation contains one or more activator(s) for a modified ecdysone receptor as described herein and one or more ligand(s) for a silent partner for the modified ecdysone receptor, as active ingredients, in admixture with an organic or inorganic carrier or excipient suitable for enteral or parenteral applications.

The active ingredients may be compounded, for example, with the usual non-toxic, pharmaceutically acceptable carriers suitable for oral, topical, nasal, transdermal, intravenous, subcutaneous, intramuscular, intracutaneous, intraperitoneally, intravascular and the like administration. Administration in the form of creams, lotions, tablets, dispersible powders, granules, syrups, elixirs, sterile aqueous or non-aqueous solutions, suspensions or emulsions, and the like, is contemplated. Exemplary pharmaceutically acceptable carriers include carriers for tablets, pellets, capsules, suppositories, solutions, emulsions, suspensions, and any other form suitable for use. Such carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. The active compound (i.e., ecdysteroid and/or retinoid as described herein) included in the pharmaceutically acceptable formulation in an amount sufficient to produce the desired effect upon the process or condition of diseases.

Pharmaceutically acceptable formulations containing the active ingredients may be in a form suitable for oral use, for example, as aqueous or oily suspensions, syrups or elixirs, tablets, troches, lozenges, dispersible powders or granules, emulsions, or hard or soft capsules. For the preparation of oral liquids, suitable carriers include emulsions, solutions, suspensions, syrups, and the like, optionally containing additives such as wetting agents, emulsifying and suspending agents, dispersing agents, sweetening, flavoring, coloring, preserving and perfuming agents, and the like. Formulations intended for oral use may be prepared according to any method known to the art for the manufacture of pharmaceutically acceptable formulations.

Tablets containing the active ingredients in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874, to form osmotic therapeutic tablets for controlled release.

In some cases, formulations for oral use may be in the form of hard gelatin capsules wherein the active ingredients are mixed with an inert solid diluent, for example, calcium carbonate, calcium phosphate or kaolin. They may also be in the form of soft gelatin capsules wherein the active ingredient is mixed with water or an oil medium, for example, peanut oil, liquid paraffin, or olive oil.

Pharmaceutically acceptable formulations may be in the form of a sterile injectable suspension. Suitable carriers include non-toxic parenterally-acceptable sterile aqueous or non-aqueous solutions, suspensions, or emulsions. Such a suspension may be formulated according to known methods using suitable dispersing or wetting agents and suspending agents. They can also be manufactured in the form of sterile water, or some other sterile injectable medium immediately before use. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. They may be sterilized, for example, by filtration through a bacteria-retaining filter, by incorporating sterilizing agents into the formulations, by irradiating the formulations, or by heating the formulations. Sterile injectable suspensions may also contain adjuvants such as preserving, wetting, emulsifying, and dispersing agents. Buffers, preservatives, antioxidants, and the like can be incorporated as required.

Compounds contemplated for use in the practice of the present invention may also be administered in the form of suppositories for rectal administration of the drug. These formulations may be prepared by mixing the drug with a suitable non-irritating excipient, such as cocoa butter, synthetic glyceride esters of polyethylene glycols, which are solid at ordinary temperatures, but liquefy and/or dissolve in the rectal cavity to release the drug.

The pharmaceutically acceptable formulations are administered in a manner compatible with the route of administration, the dosage formulation, and in a therapeutically effective amount. The required dosage will vary with the particular treatment desired, the degree and duration of therapeutic effect desired, the judgment of the practitioner, as well as properties peculiar to each individual. Moreover, suitable dosage ranges for systemic application depend on the route of administration. It is anticipated that dosages between about 10 micrograms and about 10 milligram per kilogram of body weight per day will be used for therapeutic treatment, with about 5 milligram per kilogram of body weight per day preferred.

An effective amount of the pharmaceutically acceptable formulation contemplated for use in the practice of the present invention is the amount of the pharmaceutically acceptable formulation (i.e., first and second ligand) required to achieve the desired level of transcription and/or translation of exogenous nucleic acid. A therapeutically effective amount is typically an amount of each of the first and second ligands (or precursor(s) therefor) that, when administered in a pharmaceutically acceptable formulation, is sufficient to achieve a plasma concentration of the transcribed or expressed nucleic acid product from about 0.1 $\mu$g/ml to about 100 $\mu$g/ml, preferably from about 1.0 $\mu$g/ml to about 50 $\mu$g/ml, more preferably at least about 2 $\mu$g/ml and usually 5 to 10 $\mu$g/ml.

Pharmaceutically acceptable formulations containing suitable ligand(s) are preferably administered intravenously, as by injection of a unit dose, for example. The term "unit dose," when used in reference to a pharmaceutically acceptable formulation of the present invention, refers to a quantity of the pharmaceutical formulation suitable as unitary dosage for the subject, each unit containing a predetermined quantity of active materials) calculated to produce the desired therapeutic effect in association with the required diluent, i.e., carrier, or vehicle. It may be particularly advantageous to administer such formulations in depot or long-lasting form as discussed hereinafter.

Suitable regimes for initial administration and booster shots are variable, but are typified by an initial administration followed by repeated doses at one or more intervals by a subsequent injection or other administration. Alternatively, continuous intravenous infusion sufficient to maintain concentrations in the blood in the ranges specified for in vivo therapies are contemplated.

Response elements contemplated for use in the practice of the present invention include elements recognized by the DNA-binding domain of the modified ecdysone receptor. In a preferred embodiment of the present invention, such elements are exogenous regulatory elements not normally present in the cells of the host or are native response elements which have been engineered so as to no longer be capable of binding endogenous transcription factors. One class of exogenous regulatory elements contemplated for use herein includes hormone response elements which modulate transcription of exogenous nucleic acid when bound to the DNA binding domain of the modified ecdysone receptor. Exemplary response elements include native and modified hormone response elements, GAL4 response elements, synthetic response elements (Pomerantz et al., supra), and the like. In a preferred embodiment of the present invention, modified ecdysone response elements are contemplated.

Ecdysone response elements contemplated for use in the practice of the present invention (relating to modulation of the expression of exogenous genes in a subject) include native, as well as modified ecdysone response elements. Since invention modified ecdysone receptors can function as either homodimers or as heterodimers (with a silent partner therefor), any response element that is responsive to an invention modified ecdysone receptor, in the form of a homodimer or heterodimer, is contemplated for use in the invention methods described herein. As is readily recognized by those of skill in the art, modified receptors according to the invention (whether in the form of a homodimer or a heterodimer) can bind to either a response element having an inverted repeat motif (i.e., two or more half sites in mirror image orientation with respect to one another), or to a response element having a direct repeat motif.

In a preferred embodiment of the invention, invention modified ecdysone response elements are engineered so as to no longer be capable of binding to a farnesoid hormone receptor (since the mammalian farnesoid hormone receptor is able to bind to native ecdysone receptor response element). Invention modified ecdysone response elements provide low background expression levels of the exogenous gene and increase the selectivity of the gene expression system when used in mammalian systems.

Ecdysone response elements contemplated for use herein are short cis-acting sequences (i.e., having about 12–20 bp) that are required for activation of transcription in response to an ecdysteroid, associated with a modified ecdysone receptor. The association of these response elements with otherwise ecdysone-nonresponsive regulatory sequences causes such regulatory sequences to become ecdysone responsive. Ecdysone response element sequences function in a position- and orientation-independent fashion.

The native ecdysone response element has been previously described, see, e.g., Yao et al., *Cell,* 71;63–72, 1992. Modified ecdysone response elements according to present invention comprise two half-sites (in either direct repeat or inverted repeat orientation to one another), separated by a spacer of 0–5 nucleotides. As used herein, the term "half-site" refers to a contiguous 6 nucleotide sequence that is bound by a particular member of the steroid/thyroid hormone superfamily of receptors. Each half-site is typically separated by a spacer of 0 up to about 5 nucleotides. Typically, two half-sites with a corresponding spacer make up a hormone response element. Hormone response elements can be incorporated in multiple copies into various transcription regulatory regions.

Preferred modified ecdysone response elements according to the invention comprise, in any order, a first half-site and a second half-site separated by a spacer of 0–5 nucleotides;

wherein the first and second half-sites are inverted with respect to each other;

wherein said first half-site has the sequence:

-RGBNNM-, (or complements thereof) wherein
- each R is independently selected from A or G;
- each B is independently selected from G, C, or T;
- each N is independently selected from A, T, C, or G; and
- each M is independently selected from A or C;

with the proviso that at least 4 nucleotides of each -RGBNNM- group of nucleotides are identical with the nucleotides at comparable positions of the sequence -AGGTCA-; and said second half-site is obtained from a glucocorticoid receptor subfamily response element.

The complement to the -RGBNNM- sequence set forth above is:

-YCVNNK-, wherein
- each Y is independently selected from T or C;
- each V is independently selected from C, G, or A;
- each N is independently selected from A, T, C, or G; and
- each K is independently selected from T or G.

Exemplary first half-sites having the -RGBNNM- motif for use in the invention modified ecdysone response element include, for example, half-sites selected from -AGGGCA-, -AGTTCA-, -AGGTAA-, -AGGTCA-, -GGTTCA-, -GGGTTA-, -GGGTGA-, -AGGTGA-, or -GGGTCA-. A particularly preferred first half-site is -AGTGCA-.

Glucocorticoid receptor subfamily response elements contemplated for use in the practice of the present invention are response elements having half-sites that are typically bound by glucocorticoid, mineralocorticoid, progesterone or androgen receptors. Suitable half-sites from glucocorticoid receptor subfamily response elements can be selected from the following sequence (in either orientation):

-RGNNCA- (or complements thereof such as -YCNNGT-), wherein R, Y and N are as defined above. Exemplary half-sites having the -RGNNCA- motif for use in the invention modified ecdysone response element include -AGAACA-, -GGAACA-, -AGTTCA-, -AGGTCA-, -GGAACA-, -GGTTCA-, -GGGTCA-, -GGGTCA-, -AGGTGA-, -GGGTCA-, and the like, as well as complements thereof. Particularly preferred half-sites having the -RGNNCA- motif include -AGAACA- and -GGAACA-, with -AGAACA- being especially preferred.

When the above-described modified ecdysone response elements are employed to bind invention heterodimeric receptors, the second half-site is inverted with respect to the first half-site. For example, when describing a single-strand of an invention modified ecdysone response element in the 5'-3' direction, the following general motif can be employed:

RGBNNM-(N)$_x$-TGNNCY (SEQ ID NOS:4, 13–17), where x is an integer of 0 up to about 5, with x=1 being especially preferred. As an alternative orientation to the above described response element motif (SEQ ID NO:4), an invention response element can be described in the 5'-3' direction as:

RGNNCA-(N)$_x$-KNNVCY (SEQ ID NOS:5, 18–22), where x is an integer of 0 up to about 5, with x=1 being especially preferred.

In preferred embodiments of the present invention, the first half-site is obtained from an ecdysone response element and the second half-site is obtained from a hormone response element selected from a glucocorticoid response element, a mineralocorticoid response element, a progesterone response element or an androgen response element. In a particularly preferred embodiment of the present invention, the first half-site is obtained from an ecdysone response element and the second half-site is obtained from a glucocorticoid response element.

In a particularly preferred embodiment of the invention modified ecdysone response element, the first half-site is AGTGCA and the second half-site is TGTTCT. The presently most preferred modified-ecdysone response element for use in the invention methods is:

AGTGCA-N-TGTTCT (SEQ ID NO:6).

In another aspect of the invention, when modified ecdysone receptors of the invention exist as homodimers, response elements employed preferably have a direct repeat motif (instead of the above-described inverted repeat motif), as follows:

RGBNNM-(N)$_x$-RGBNNM (SEQ ID NOS:7, 23–27), where R, B, N and M are as previously defined, and x' is an integer of 0 up to about 5, with x'=3 being especially preferred.

Invention modified ecdysone response elements are characterized as having substantially no constitutive activity, which refers to the substantial absence of background levels of gene expression initiated by invention modified ecdysone response elements when introduced into mammalian expression systems. Since it has been found that mammalian farnesoid hormone receptors are able to bind to and transactivate gene expression from native ecdysone response elements, in certain embodiments of the present invention (e.g., where it is desired to avoid farnesoid-mediated background expression), modified ecdysone response elements are employed (because such response elements typically have substantially no binding affinity for farnesoid X receptor (FXR).

Presently preferred invention modified ecdysone response elements are further characterized as having substantially no binding affinity for farnesoid X receptor (FXR), i.e., invention response elements are incapable of binding FXR (which would thereby create undesired background levels of expression). Thus, presently preferred invention modified ecdysone response elements preferably induce basal levels of expression of substantially zero.

Response elements employed in the practice of the present invention are operably linked to a suitable promoter for expression of exogenous gene product(s). As used herein, the term "promoter" refers to a specific nucleotide sequence recognized by RNA polymerase, the enzyme that initiates RNA synthesis. This sequence is the site at which transcription can be specifically initiated under proper conditions. When exogenous genes, operatively linked to a suitable promoter and ecdysone response elements, are introduced into the cells of a suitable host, expression of the exogenous genes is controlled by the presence of ecdysteroid compounds, which are not normally present in the host cells.

In accordance with another embodiment of the present invention, there are provided methods of inducing the expression of an exogenous gene in a mammalian subject containing:

(i) a DNA construct comprising an exogenous gene operatively associated with a response element, (ii) DNA encoding a modified ecdysone receptor under the control of an inducible promoter; wherein said modified ecdysone receptor, in the optional presence of a receptor capable of acting as a silent partner therefor, is capable of binding to said response element, and (iii) a first ligand and a second ligand, wherein said first ligand is:

a ligand for said modified ecdysone receptor, not normally present in the cells of said subject, and not toxic to said subject; and wherein said second ligand is a ligand for said silent partner;

said method comprising subjecting said subject to conditions suitable to induce expression of said modified ecdysone receptor.

Inducible promoters contemplated for use in the practice of the present invention are transcription regulatory regions that do not function to transcribe mRNA unless inducing conditions are present. Examples of suitable inducible promoters include DNA sequences corresponding to: the *E. coli* lac operator responsive to IPTG (see Nakamura et al., *Cell*, 18:1109–1117, 1979); the metallothionein promoter metal-regulatory-elements responsive to heavy-metal (e.g. zinc) induction (see Evans et. al, U.S. Pat. No. 4,870,009), the phage T7lac promoter responsive to IPTG (see Studier et al., *Meth. Enzymol.*, 185: 60–89, 1990; and U.S. Pat. No. 4,952,496), the heat-shock promoter, and the like.

In accordance with another embodiment of the present invention, there are provided methods of inducing expression of an exogenous gene in a mammalian subject containing a DNA construct comprising said exogenous gene under the control of a response element, said method comprising introducing into said subject:

a modified ecdysone receptor;

a first ligand; and a second ligand, wherein said first ligand is:

a ligand for said modified ecdysone receptor, not normally present in the cells of said subject, and not toxic to said subject; and wherein said second ligand is a ligand for said silent partner;

wherein said receptor, optionally in combination with a receptor capable of acting as a silent partner therefor, and ligand(s) therefor, binds to said response element, activating transcription therefrom.

In accordance with another embodiment of the present invention, there are provided methods for the expression of recombinant products detrimental to a host organism, said method comprising:

transforming suitable host cells with:

(i) a DNA construct encoding said recombinant product operatively associated with a response element, and (ii) DNA encoding a modified ecdysone receptor, wherein said modified ecdysone receptor forms a homodimer, or a heterodimer with a silent partner therefor;

growing said host cells in suitable media; and inducing expression of said recombinant product by introducing into said host cells a first ligand and a second ligand, wherein said first ligand is:

a ligand for said modified ecdysone receptor, not normally present in the cells of said subject, and not toxic to said subject; and wherein said second ligand is a ligand for said silent partner component of said heterodimer; and optionally introducing into said host cells a receptor capable of acting as a silent partner for said modified ecdysone receptor.

Recombinant products detrimental to a host organism contemplated for expression in accordance with the present invention include any gene product that functions to confer a toxic effect on the organism. For example, inducible expression of a toxin such as the diptheroid toxin would allow for inducible tissue specific ablation (Ross et al. (1993) *Genes and Development* 7, 1318–1324). Thus, the numerous gene products that are known to induce apoptosis in cells expressing such products are contemplated for use herein (see, e.g., *Apoptosis, The Molecular Basis of Cell Death*, Current Communications In Cell & Molecular Biology, Cold Spring Harbor Laboratory Press, 1991).

Suitable media contemplated for use in the practice of the present invention include any growth and/or maintenance media, but exclude first and second ligand as described above.

In accordance with another embodiment of the present invention, there are provided nucleic acids encoding modified ecdysone receptors as described herein. Such nucleic acids can be incorporated into various expression vectors known to those of skill in the art. Preferred nucleic acids encode constructs described in FIG. 1D.

In accordance with another embodiment of the present invention, there are provided gene transfer vectors useful for the introduction of invention constructs into suitable host cells. Such gene transfer vectors comprise a transcription regulatory region having a minimal promoter (i.e., a promoter region that does not have an enhancer), and an invention modified ecdysone response element, wherein said regulatory region is operatively associated with DNA containing an exogenous gene, and wherein said modified ecdysone response element is present in multiple copies. The number of copies of response elements can readily be varied by those of skill in the art. For example, transcription regulatory regions can contain from 1 up to about 50 copies of a particular response element, preferably 2 up to about 25 copies, more preferably 3 up to about 10–15 copies, with about 4–6 copies being especially preferred.

Gene transfer vectors (also referred to as "expression vectors") contemplated for use herein are recombinant nucleic acid molecules that are used to transport exogenous nucleic acid into cells for expression and/or replication thereof. Expression vectors may be either circular or linear, and are capable of incorporating a variety of nucleic acid constructs therein. Expression vectors typically come in the form of a plasmid that, upon introduction into an appropriate host cell, results in expression of the inserted DNA.

As used herein, the phrase "transcription regulatory region" refers to the region of a gene or expression construct that controls the initiation of mRNA transcription. Regulatory regions contemplated for use herein typically comprise at least a minimal promoter in combination with an ecdysone response element. A minimal promoter, when combined with an enhancer region (e.g., a hormone response element), functions to initiate mRNA transcription in response to a ligand/receptor complex. However, transcription will not occur unless the required inducer (ligand) is present.

As used herein, the phrase "operatively associated with" refers to the functional relationship of DNA with regulatory and effector sequences of nucleotides, such as promoters, enhancers, transcriptional and translational stop sites, and other signal sequences. For example, operative linkage of DNA to a promoter refers to the physical and functional relationship between the DNA and promoter such that the transcription of such DNA is initiated from the promoter by an RNA polymerase that specifically recognizes, binds to and transcribes the DNA.

Preferably, the transcription regulatory region further comprises a binding site for at least one ubiquitous transcription factor. Such a binding site is preferably positioned between the promoter and modified ecdysone response element of the invention. Suitable ubiquitous transcription factors for use herein are well-known in the art and include, for example, Sp1.

Expression vectors suitable for use in the practice of the present invention are well known to those of skill in the art and include those that are replicable in eukaryotic cells and/or prokaryotic cells as well as those that remain episomal and those that integrate into the host cell genome. Expression vectors typically further contain other functionally important nucleic acid sequences, such as expression constructs encoding antibiotic resistance proteins, and the like.

Exemplary eukaryotic expression vectors include eukaryotic constructs, such as the pSV-2 gpt system (Mulligan et al., Nature, 1979, 277:108–114); pBlueScript (Stratagene, La Jolla, Calif.), the expression cloning vector described by Genetics Institute (Science, 1985, 228;810–815), and the like. Each of these plasmid vectors are capable of promoting expression of the invention chimeric protein of interest.

Promoters, depending upon the nature of the regulation, may be constitutively or inducibly regulated, or may be tissue-specific (e.g., expressed only in T-cells, endothelial cells, smooth muscle cells, and the like). Exemplary promoters contemplated for use in the practice of the present invention include the SV40 early promoter, the cytomegalovirus (CMV) promoter, the mouse mammary tumor virus (MMTV) steroid-inducible promoter, Moloney murine leukemia virus (MMLV) promoter, elongation factor 1α (EF1α) promoter, albumin promoter, APO A1 promoter, cyclic AMP dependent kinase II (CAMKII) promoter, kevatin promoters, CD3 promoter, immunoglobulin light or heavy chain promoters, neurofilament promoter, neuron specific enolase promoter, L7 promoter, CD2 promoter, myosin light chain kinase promoter, HOX gene promoter, thymidine kinase (TK) promoter, RNA Pol II promoter, MYOD promoter, MYF5 promoter, phophoglycerokinase (PGK) promoter, Stf1 promoter, Low Density Lipoprotein (LDL) promoter, and the like.

Suitable means for introducing (transducing) expression vectors containing invention nucleic acid constructs into host cells to produce transduced recombinant cells (i.e., cells containing recombinant heterologous nucleic acid) are well-known in the art (see, for review, Friedmann, 1989, Science, 244:1275–1281; Mulligan, 1993, Science, 260:926–932, each of which are incorporated herein by reference in their entirety). Exemplary methods of transduction include, e.g., infection employing viral vectors (see, e.g., U.S. Pat. Nos. 4,405,712 and 4,650,764), calcium phosphate transfection (U.S. Pat. Nos. 4,399,216 and 4,634,665), dextran sulfate transfection, electroporation, lipofection (see, e.g., U.S. Pat. Nos. 4,394,448 and 4,619,794), cytofection, particle bead bombardment, and the like. Heterologous nucleic acid(s) contained within expression vectors can optionally include sequences which allow for extrachromosomal (i.e., episomal) maintenance, or the heterologous nucleic acid can be donor nucleic acid that integrates into the genome of the host.

In a specific embodiment, said expression transfer vector is a viral vector, preferably a retroviral vector. Retroviral vectors are gene transfer plasmids wherein the heterologous nucleic acid resides between two retroviral LTRs. Retroviral vectors typically contain appropriate packaging signals that enable the retroviral vector, or RNA transcribed using the retroviral vector as a template, to be packaged into a viral virion in an appropriate packaging cell line (see, e.g., U.S. Pat. No. 4,650,764).

Suitable retroviral vectors for use herein are described, for example, in U.S. Pat. Nos. 5,399,346 and 5,252,479; and in WIPO publications WO 92/07573, WO 90/06997, WO 89/05345, WO 92/05266 and WO 92/14829, incorporated herein by reference, which provide a description of methods for efficiently introducing nucleic acids into human cells using such retroviral vectors. Other retroviral vectors include, for example, mouse mammary tumor virus vectors (e.g., Shackleford et al., 1988, PNAS, USA, 85:9655–9659), lentiviruses, and the like.

Various procedures are also well-known in the art for providing helper cells which produce retroviral vector particles which are essentially free of replicating virus. See, for example, U.S. Pat. No. 4,650,764; Miller, Human Gene Therapy, 1:5–14 (1990); Markowitz, et al., Journal of Virology, 61(4):1120–1124 (1988); Watanabe, et al., Molecular and Cellular Biology, 3(12):2241–2249 (1983); Danos, et al., Proc. Natl. Acad. Sci., 85:6460–6464 (1988); and Bosselman, et al., Molecular and Cellular Biology, 7(5):1797–1806 (1987), which disclose procedures for producing viral vectors and helper cells which minimize the chances for producing a viral vector which includes a replicating virus.

Recombinant retroviruses suitable for carrying out the invention methods are produced employing well-known methods for producing retroviral virions. See, for example, U.S. Pat. No. 4,650,764; Miller, Human Gene Therapy, 1:5–14 (1990); Markowitz, et al., Journal of Virology, 61(4):1120–1124 (1988); Watanabe, et al., Molecular and Cellular Biology, 3(12):2241–2249 (1983); Danos, et al., Proc. Natl. Acad. Sci., 85:6460–6464 (1988); and Bosselman, et al., Molecular and Cellular Biology, 7(5):1797–1806 (1987).

In accordance with another embodiment of the present invention, there are provided recombinant cells containing nucleic acid encoding modified ecdysone receptors as described herein optionally further containing expression constructs. Exemplary eukaryotic cells suitable for introducing invention expression vectors include, e.g., CV-1 cells, P19 cells and NT2/D1 cells (which are derived from human embryo carcinomas), ES cells (embryonic stem cells), COS cells, mouse L cells, Chinese hamster ovary (CHO) cells, primary human fibroblast cells, human embryonic kidney cells, African green monkey cells, HEK 293 (ATCC accession #CRL 1573; U.S. Pat. No. 5,024,939), Ltk⁻ cells (ATCC accession #CCL1.3), COS-7 cells (ATCC under accession #CRL 1651), DG44 cells (dhfr⁻ CHO cells; see, e.g., Urlaub et al. (1986) Cell. Molec. Genet. 12: 555), cultured primary tissues, cultured tumor cells, and the like. Presently preferred cells include CV-1 and 293 cells.

In accordance with another embodiment of the present invention, there is provided a transgenic animal containing a nucleic acid encoding an invention modified ecdysone receptor. As used herein, the phrase "transgenic animal" refers to an animal that contains one or more inheritable expression constructs containing a recombinant modified ecdysone receptor transgene and/or an exogenous gene under the transcription control of an invention modified ecdysone response element. Preferably, an invention transgenic animal also contains one or more inheritable expression constructs containing a member of the steroid/thyroid hormone superfamily of receptors that functions as a silent partner for modified ecdysone receptor (e.g., RXR).

Methods of making transgenic animals using a particular nucleic acid construct are well-known in the art. When preparing invention transgenic animals, it is preferred that two transgenic lines are generated. The first line will express, for example, RXR and a modified EcR (e.g., VpEcR). Tissue specificity is conferred by the selection of tissue-specific promoters (e.g., T-cell specific) that will then direct the expression of the receptors. A second line contains an ecdysone responsive promoter controlling the expression of an exogenous cDNA.

In a preferred embodiment of the present invention, an invention transgenic animal contains one or more expression constructs containing nucleic acid encoding a modified ecdysone receptor, and an exogenous gene under the transcription control of an invention modified ecdysone response element, and optionally, exogenous RXR. It has been found that in transgenic mice containing an ecdysone inducible promoter (i.e., an invention modified ecdysone response element) and expressing a modified ecdysone receptor and RXR, treatment with a first and a second ligand (as described herein) can activate gene expression. Thus, with tissue specific expression of the modified ecdysone receptor and RXR and timely ligand addition, inducible gene expression can be achieved with spatial, dosage, and temporal specificity.

In accordance with another embodiment of the present invention, there are provided methods for inducing expression of an exogenous gene in a transgenic animal containing a modified ecdysone receptor as described herein, said method comprising:

introducing into said animal a DNA construct encoding an exogenous gene under the transcription control of a response element responsive to said modified ecdysone receptor; and administering to said animal an amount of a first ligand and a second ligand (as described herein) effective to induce expression of said exogenous gene.

As discussed hereinbefore, the modified ecdysone receptor forms a homodimer, or optionally a heterodimer in the presence of a silent partner of the steroid/thyroid hormone superfamily of receptors, and functions to activate transcription from an expression vector having a response element responsive to the particular homodimer or heterodimer formed.

In accordance with another embodiment of the present invention, there are provided methods for the induction of two different genes in a mammalian subject comprising: activating a first exogenous gene employing the invention ecdysone inducible system; and activating a second gene using an inducible gene expression system. Examples of inducible gene expression systems include gene expresssion induced by tetracycline (i.e., tetracycline-inducible gene expression), mammalian steroid hormones or synthetic steroids thereof (i.e, RU-486-inducible gene expression), chemical inducer of dimerization (e.g., FK506, FK1012, CsA, rapamycin, FKCsA, and the like; see, e.g., Rivera et al., *Nat Med* 2:1028–1032, 1996), and the like. The invention method for inducing two different genes is particularly advantageous because it permits the temporal, spatial, and dosage specific control of two exogenous genes.

The tetracycline inducible system is well-known in the art (see, e.g., Gossen et al. (1992) *Proc. Natl. Acad. Sci.* 89, 5547–5551; Gossen et al.(1993) *TIBS* 18, 471–475; Furth et al. (1994) *Proc. Natl. Acad. Sci.* 91, 9302–9306; and Shockett et al. (1995) *Proc. Natl. Acad. Sci.* 92, 6522–6526).

All U.S. and Foreign Patent publications, textbooks, and journal publications referred to herein are hereby expressly incorporated by reference in their entirety. The invention will now be described in greater detail by reference to the following non-limiting examples.

EXAMPLE 1

Preparation of Modified Ecdysone Receptors
Plasmid Preparation

The plasmids CMX-EcR, CMX-USP, CMX-FXR, CMX-hRXRα, EcREx5-ΔMTV-Luc, CMX-GEcR, MMTV-luc, and CMX-GR have been previously described (Yao, et al., *Nature* 366:476–479 (1993) and Forman, et al. *Cell* 81:687–693 (1995)).

The plasmid CMX-VpEcR was constructed by ligation of an EcoRI fragment of psk-EcR and CMM-Vp16.

The plasmid CMX-VgEcR was generated by site-directed mutagenesis of CMX-VpEcR using the Transformer Mutagenesis Kit (Clontech) and the mutagenic Oligonucleotide (SEQ ID NO:8):
5'-TACAACGCCCTCACCTGTGGATCCTGCAAGG
TGTTTCTTTCGACGCAGC-3'.

Mutagenesis of VpEcR to VgEcR altered the P-box region of the DNA binding domain of ecdysone receptor to resemble that of GR (Umesono and Evans, *Cell* 57:1139–1146 (1989)). The following amino acids in the DNA-binding domain of the ecdysone receptor were altered: E282G, G283S, and G286V (E=glutamate, G=glycine, S=serine, V=valine).

The reporter construct EcREx4-ΔHSP-β-gal was constructed by oligomerizing two annealed oligonucleotides containing the HSP-EcRE (Yao, et al., *Nature* 366:476–479 (1993)).

EcREx4-Sp1x3-ΔHSP-βgal was constructed by ligating the following annealed oligonucleotides into the Asp718 site of EcREx4-HSP-β-gal (SEQ ID NO:9):
5'-GTACTCCCGGGGCGGGGCTATGCGGGGCGGGG
CTAATCGCTAGGGGCGGGGCA-3'
and (SEQ ID NO:10):
5'-GTACTGCCCCGCCCCTAGCGATTAGCCCCGCC
CCGCATAGCCCCGCCCCGGGA-3'.

ΔHSP is a minimal promoter derived from the Drosophila heat shock promoter with its enhancers deleted.

To generate the construct E/GREx4-ΔMTV-Luc, the following oligonucleotides (SEQ ID NO:11):
5'-AGCTCGATGGACAAGTGCATTGTTCTTTGCTGAA-3';
and (SEQ ID NO:12):
5'-AGCTTTCAGCAAGAGAACAATGCACTTGTCCATCG-3',
were annealed, multimerized, and ligated into the HindIII site of ΔMTV-Luc. The resulting reporter contained 4 copies of the invention modified ecdysone response element E/GRE.

To produce the plasmid pRC-ESHβ, a BglII/(XhoI) fragment containing EcREx4-Sp1x3-ΔHSP-β-gal was subcloned into BglII/(NotI) digested PRC-CMV (Invitrogen, San Diego, Calif.), which contains a neomycin resistance gene.

Cell Culture and Transient Transfections

CV-1 cells were maintained in DMEM supplemented with 10% Fetal Bovine serum. Transient transfections were performed using DOTAP transfection reagent (Boehringer-Mannheim). Transfections using β-galactosidase as the reporter were assayed either by Galactolight luminescent assay (Tropix, Bedford, Mass.) or by standard liquid ONPG assay (Sigma, St. Louis, Mo.). The values were normalized by co-transfection of CMX-luciferase. Transfections using luciferase as the reporter were assayed by standard techniques using luciferin and ATP. These values were normalized by co-transfection of CMX-β-galactosidase. Hormone treated cells were treated with ethanol, 50 μM Juvenile Hormone III (Sigma), 1 μM muristerone A (Zambon, Bresso, IT), or 1 μM dexamethasone (Sigma) unless otherwise noted.

Figure 1A:
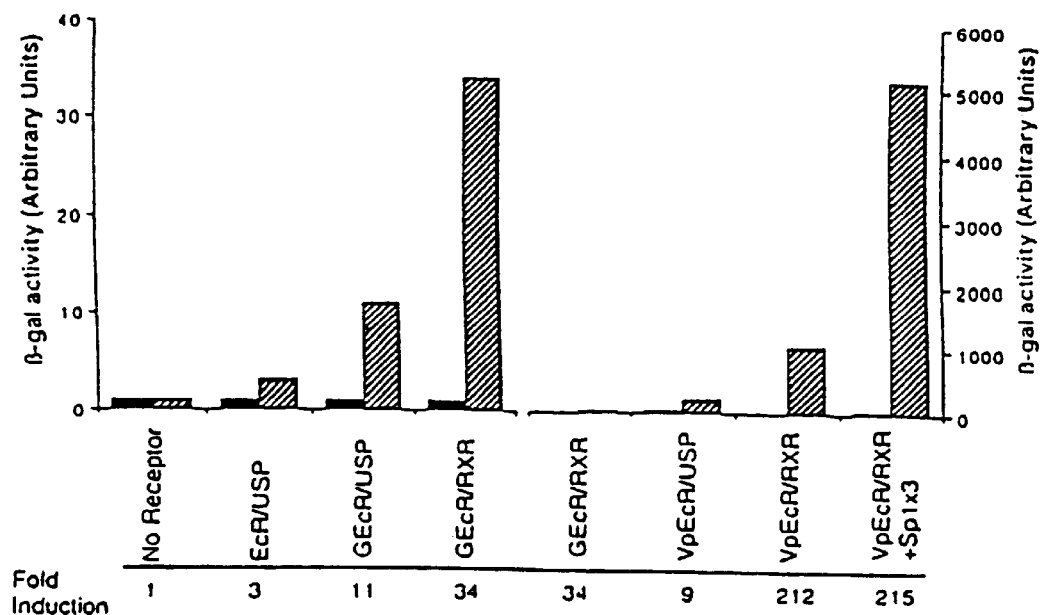
FIGS. 1A–1D show the effect on ecdysone responsiveness of using various combinations of USP or RXR with different modified EcRs.

To maximize the sensitivity of the invention ecdysone inducible system, modifications of the ecdysone receptor were made. The N-terminal transactivation domain of the ecdysone receptor was replaced by the corresponding domain of the glucocorticoid receptor (GR), resulting in the modified ecdysone receptor GEcR (See FIG. 1D). CV-1 cells were transfected with the plasmid CMX-GEcR encoding the modified ecdysone receptor as discussed above. After transfection, cells were either treated with ethanol or 1 μM muristerone A. This hybrid modified ecdysone receptor boosted muristerone responsiveness from 3- to 11-fold in a transient transfection assay (FIG. 1A). Replacement of the natural heterodimeric partner for the ecdysone receptor, USP, by its mammalian homologue, the retinoid X receptor (RXR), produced a more potent ligand dependent heterodimer, providing a 34 fold induction (FIG. 1A).

Figure 1B:
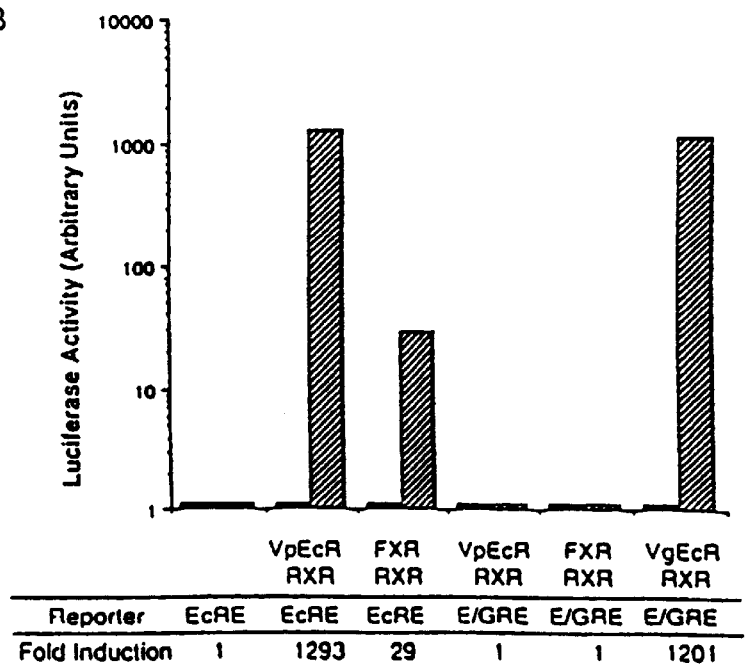
Figure 1C:
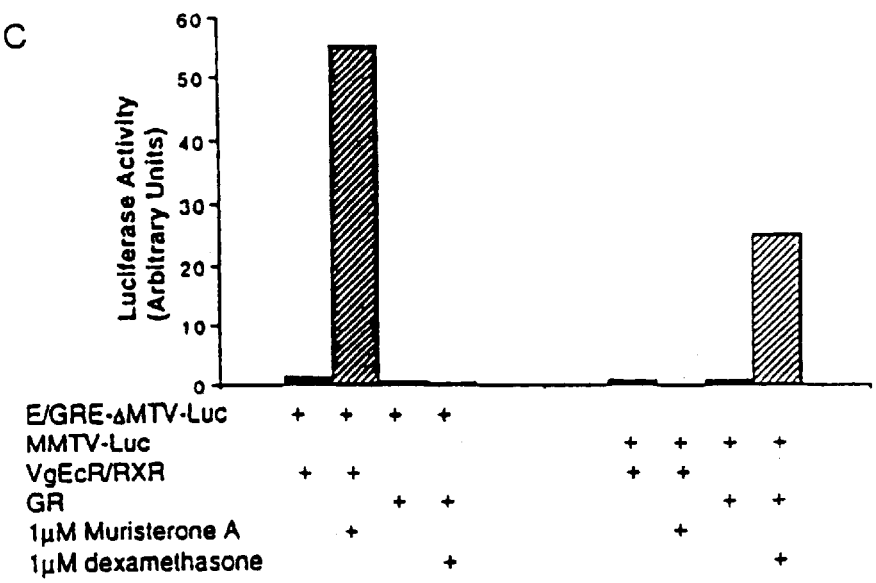
Figure 1D:
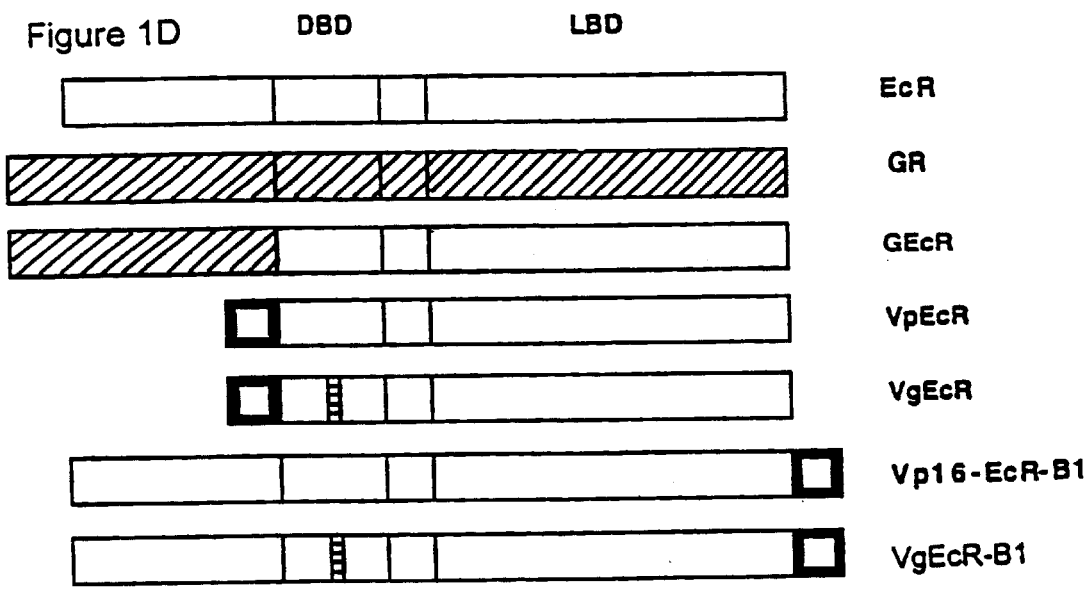

A more potent heterodimer, however, was obtained by combining RXR and VpEcR, an N-terminal truncation of the ecdysone receptor attached to the VP16 activation domain, resulting in a 212 fold induction (FIGS. 1A and 1D). Different from most nuclear receptor/VP16 fusion proteins which exhibit high constitutive activity, VpEcR generates ligand dependent superinduction while maintaining a very low basal activity (Underhill et al., *Mol. Encod.* 8:274–285 (1994) and Perlmann et al., *Genes & Devel.* 7:1411–1422 (1993))

In addition, the reporter vector was also modified by inserting consensus binding sites for the ubiquitous transcription factor Sp1 between the minimal promoter and the ecdysone response elements (Kamine et al., *Proc. Natl. Acad. Sci.* 88:8510–8514 (1991) and Strahle et al., *EMBO* 7:3389–3395 (1988)). The addition of Sp1 sites to the ecdysone responsive promoter increases the absolute activity 5-fold (FIG. 1A).

EXAMPLE 2

Construction of a Novel Ecdysone Response Element

Although no mammalian transcription factors have been shown to have a natural enhancer element like the ecdysone response element, which is composed of two inverted half-sites of the sequence AGGTCA spaced by one nucleotide, it is difficult to preclude such a possibility. The recently cloned farnesoid X receptor (FXR) can very weakly activate certain synthetic promoters containing an ecdysone response element in response to extremely high concentrations of farnesoids (Forman et al., *Cell* 81:687–693 (1995)).

In FXR containing cells and in transgenic mice, activation of gene expression by endogenous receptors would create undesirable background levels of reporter protein. To circumvent this potential problem, the DNA binding specificity of VpEcR was altered to mimic that of GR, which binds as a homodimer to an inverted repeat of the sequence AGAACA, spaced by three nucleotides. This altered binding specificity was achieved by mutating three amino acid residues of VpEcR in the P-box of the DNA binding domain, a region previously shown to be essential for DNA sequence recognition (Umesono and Evans, *Cell* 57:1139–1146 (1989)). This new hybrid modified ecdysone receptor is referred herein as VgEcR and is responsive to a new hybrid respone element referred to herein as the E/GRE (SEQ ID NO:6), which contains two different half-site motifs, RGBNNM and RGNNCA, spaced by one nucleotide (FIG. 1B). This new response element is a hybrid between the glucocorticoid response element (GRE) and that of type II nuclear receptors like RXR, EcR, retinoic acid receptor (RAR), thyroid hormone receptor (T3R), etc. Although FXR can activate a promoter containing the wild type ecdysone response element, it cannot activate one containing the E/GRE (FIG. 1B; note log scale). The E/GRE reporter is not activated by GR nor does VgEcR activate a dexamethasone responsive promoter (FIG. 1C).

EXAMPLE 3

Assay for Inducer Effectiveness on the Ecdysone-inducible Expression System

CV-1 cells were maintained in DMEM supplemented with 10% fetal bovine serum. Transfections were performed using the Dotap transfection reagent (Boehringer Mannheim). All candidate inducers were dissolved in either ethanol or DMSO. Muristerone A (MurA) was used as a positive control for activation. All transfections were performed in triplicate.

Subconfluent CV-1 cells were transiently transfected with plasmids encoding the basic components of the invention ecdysone-inducible system (e.g., the VgEcR/RXR heterodimer) under the control of a strong constitutive promoter (e.g., CMX). The E/GRE$_4$-ΔMTV-Luc plasmid is routinely used as a reporter. This plasmid (see No et al., in *Proc. Natl. Acad. Sci. USA* 93:3346 (1996)) contains the firefly luciferase gene under the control of a minimal promoter and four binding sites for the VgEcR/RXR heterodimer. A CMX-β-gal reporter plasmid was included in the transfection as a control for transfection efficiency. Approximately 10 hours after transfection, the media was removed and replaced with fresh media containing varying concentrations of the putative inducers. Cells were exposed to candidate activators for 20–48 hours, then assayed for luciferase and β-galactosidase activity employing standard techniques. Luciferase values were normalized using β-galactosidase activity levels.

FIG. 3 presents the results of testing with muristerone A alone over several concentrations, an RXR ligand (6-(1-(3, 5,5,8,8-pentamethyl-5,6,7,8-tetrahydronaphthalen-2-yl)cyclopropyl)nicotinic acid (LG1000268)) alone over several concentrations, or a combination of the two, where the concentration of MurA varies while the concentration of LG1000268 remains constant (100 nM).

The results presented in FIG. 3 illustrate that RXR ligand alone has substantially no effect on this system, that muristerone alone is an effective inducer of the system, and that the combination of muristerone and RXR ligand dramatically enhances the activation of the system.

EXAMPLE 4

Assays with Inducers Other than Muristerone

The benefits of combining ecdysone inducers with RXR agonists were further demonstrated employing other ecdysone agonists, besides muristerone. Thus, the procedure described in Example 3 was repeated with two different diacylhydrazines, i.e., N'-(3,5-dimethylbenzoyl)-N-(2- methyl-3,4-(ethylenedioxy)benzoyl)-N'-(tert-butyl) hydrazine and N'-(3,5-dimethylbenzoyl)-N-(4-ethylbenzoyl)-N'-(tert-butyl)hydrazine (FIG. 4). The enhanced ability of these compounds to activate the invention expression system in the further presence of an RXR agonist (e.g., (6-(1-(3,5,5,8,8-pentamethyl-5,6,7,8-tetrahydronaphthalen-2-yl)cyclopropyl)nicotinic acid (LG1000268)) is readily apparent upon inspection of the data presented in FIG. 4.

EXAMPLE 5

Effect of Various RXR Ligands on Induction Activity of Ponasterone A

The benefits of combining ecdysone inducers with RXR agonists were further demonstrated employing the ecdysone analog, ponasterone A (ponA), in combination with several different RXR agonists. Thus, the procedure described in Example 3 was repeated with ponasterone A and three different RXR agonists, i.e., LG1000268 ((6-(1-(3,5,5,8,8-pentamethyl-5,6,7,8-tetrahydronaphthalen-2-yl) cyclopropyl)nicotinic acid), LGD 1069 (4-(1-(3,5,5,8,8-pentamethyl-5,6,7,8-tetrahydro-2-naphthyl)-ethenyl) benzoic acid) and 9-cis-RA(9-cis-retinoic acid). The enhanced ability of each of these RXR agonists to activate the invention expression system in combination with ponasterone A, is readily apparent upon inspection of the data presented in FIG. 5.

While the invention has been described in detail with reference to certain preferred embodiments thereof, it will be understood that modifications and variations are within the spirit and scope of that which is described and claimed.

That which is claimed is:

1. A formulation comprising:

at least one ecdysteroid which is an activator for a modified ecdysone receptor, at least one RXR or USP agonist which is an activator for a silent partner for said modified ecdysone receptor, and a pharmaceutically acceptable carrier;

wherein said modified ecdysone receptor comprises:
a ligand binding domain capable of binding an ecdysteroid;
a DNA-binding domain; and
an activation domain, wherein at least one of said DNA-binding domain or said activation domain is not obtained from a native ecdysone receptor wherein said silent partner is RXR or USP, and wherein said modified ecdysone receptor forms a heterodimer with said RXR or USP.

2. formulation according to claim 1 wherein said pharmaceutically acceptable carrier renders said formulation suitable for oral, topical, nasal, transdermal, intravenous, subcutaneous, intramuscular, intracutaneous, intraperitoneal or intravascular administration.

3. A formulation according to claim 1 wherein said ecdysteroid is a naturally occurring ecdysone, an ecdysone-analog or an ecdysone-mimic.

4. A formulation according to claim 3 wherein said naturally occurring ecdysone is α-ecdysone or β-ecdysone.

5. A formulation according to claim 3 wherein said ecdysone analog is ponasterone A, ponasterone B, ponasterone C, ponasterone D, 26-iodoponasterone A, muristerone A, inokosterone, 26-mesylinokosterone, sidasterone, buterosterone, ajugasterone, makisterone, cyasterone or sengosterone.

6. A formulation according to claim 3 wherein said ecdysone-mimic is a 1,2-diacyl hydrazine, an N'-substituted-N,N'-disubstituted hydrazine, a dibenzoylalkyl cyanohydrazine, an N-substituted-N-alkyl-N,N-diaroyl hydrazine, an N-substituted-N-acyl-N-alkyl, carbonyl hydrazine, an N-aroyl-N'-alkyl-N'-aroyl hydrazine, a 3,5-dialkyl-4-hydroxy-N-alkyl-benzamide, or an 8-O-acetylharpagide.

7. A formulation according to claim 3 wherein said ecdysone-mimic has the formula:

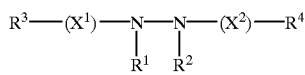

wherein:
- R$^1$ is optionally hydrogen, lower alkyl or substituted lower alkyl, alkenyl or substituted alkenyl, alkynyl or substituted alkynyl, aryl or substituted aryl, or heteroaryl or substituted heteroaryl, with the proviso that R$^1$ is not present when X$^1$ is part of a carbon-nitrogen double bond linking R$^3$ to the hydrazino group;
- R$^2$ is optionally hydrogen, alkyl or substituted alkyl, or cyclohexyl or substituted cyclohexyl, with the proviso that R$^2$ is not present when X$^2$ is part of a carbon-nitrogen double bond linking R$^4$ to the hydrazino group;
- R$^3$ and R$^4$ are independently part of an appropriately substituted carbon-nitrogen double bond which links R$^3$ and/or R$^4$ to the hydrazino linkage, or R$^3$ and R$^4$ are independently aryl or substituted aryl, heteroaryl or substituted heteroaryl, provided, however, that when two adjacent positions on the aryl or heteroaryl moieties are substituted with alkoxy, thioalkyl, alkylamino, or dialkylamino groups, these groups may be joined to form a 5- or 6-membered heterocyclic ring system, or R$^3$ and R$^4$ are independently heterocyclic or substituted heterocyclic, or cycloalkyl or substituted cycloalkyl; and
- X$^1$ and X$^2$ are independently —C(O)—, —C(S)—, —C(NR$_2$)—, —C(=CN)NH—, —C(O)O—, —C(O)NH—, —C(O)NHSO$_2$—, —CH$_2$—, —SO$_2$—, —P(O)CH$_3$—, or an appropriate substituted carbon-nitrogen double bond which links R$^3$ and/or R$^4$ to the hydrazino linkage.

8. A formulation according to claim 3 wherein said ecdysone-mimic is N'-(3,5-dimethylbenzoyl)-N-(4-ethylbenzoyl)-N'-(tert-butyl)hydrazine, N,N'-dibenzoyl-N'-(tert-butyl) hydrazine, N'-(3,5-dimethylbenzoyl)-N-(4-ethylbenzyl)-N'-(tert-butyl)hydrazine, N'-(3,5-dimethylbenzoyl)-N-(2-methyl-3,4-(ethylenedioxy)-benzoyl)-N'-(tert-butyl)hydrazine, 3,5-di-tert-butyl-4-hydroxy-N-isobutyl-benzamide or 8-O-acetylharpagide.

9. A formulation according to claim 1 wherein said activator for said silent partner is an RXR agonist.

10. A formulation according to claim 9 wherein said RXR agonist is 9-cis-retinoic acid, 4-(1-(3,5,5,8,8-pentamethyl-5,6,7,8-tetrahydro-2-naphthyl)-ethenyl)benzoic acid, ((E)-2-(2-(5,6,7,8-tetra-hydro-3,5,5,8,8-penta-methyl-2-naphthyl)propen-1-yl)-4-thiophenecarboxylic acid, 2-(5,6,7,8-tetrahydro-5,5,8,8-tetramethyl-2-naphthyl)-2-(carboxyphenyl)-1,3-dioxolane, 4-(5H-2,3-(2,5-dimethyl-2,5-hexano)-5-methyldibenzo(b,e) (1,4)diazepin-11-yl)-benzoic acid or thiadiazepin analogs thereof, 3,7,11,15-tetramethyl hexadecanoic acid(phytanic acid), 6-(1-(3,5,5,8,8-pentamethyl-5,6,7,8-tetrahydronaphthalen-2-yl)cyclopropyl)nicotinic acid, 2-(4-carboxyphenyl)-2-(5,6,7,8-tetrahydro-5,5,8,8-tetramethyl-2-naphthalenyl-1,3-dithiane or 4-(2-methyl)-1-(5,6,7,8-tetrahydro-5,5,8,8-tetramethyl-2-naphthalenyl)propenyl)benzoic acid.

11. A formulation according to claim 9 wherein said RXR agonist is LG1000268 or LGD 1069.

12. A kit comprising:
- at least one ecdysteroid which is an activator for a modified ecdysone receptor,
- at least one RXR or USP agonist which is an activator for a silent partner for said modified ecdysone receptor, and
- a pharmaceutically acceptable carrier;
  wherein said modified ecdysone receptor comprises:
    a ligand binding domain capable of binding an ecdysteroid;
  a DNA-binding domain; and
  an activation domain,
    wherein at least one of said DNA-binding domain or said activation domain is not obtained from a native ecdysone receptor wherein said silent partner is RXR or USP, and
  wherein said modified ecdysone receptor forms a heterodimer with said RXR or USP.

13. A kit according to claim 12, wherein said activator for silent partner is RXR agonist.

14. A kit according to claim 12 wherein said ecdysteroid is selected from the group consisting of a naturally occurring ecdysone, an ecdysone-analog and an ecdysone-mimic.

* * * * *

SEQUENCE LISTING

```
<160> NUMBER OF SEQ ID NOS: 27

<210> SEQ ID NO 1
<211> LENGTH: 71
<212> TYPE: PRT
<213> ORGANISM: Artificial Sequence
<220> FEATURE:
<221> NAME/KEY: misc_feature
<223> OTHER INFORMATION: Binding domain of the steroid/thyroid hormone
      superfamily of receptor
<221> NAME/KEY: VARIANT
<222> LOCATION: (1)..(71)
<223> OTHER INFORMATION: Xaa is any amino acid

<400> SEQUENCE: 1

Cys Xaa Xaa Cys Xaa Xaa Asp Xaa Ala Xaa Gly Xaa Tyr Xaa Xaa Xaa
1               5                   10                  15

Xaa Cys Xaa Xaa Cys Lys Xaa Phe Phe Xaa Arg Xaa Xaa Xaa Xaa Xaa
            20                  25                  30

Xaa Xaa Xaa Xaa Xaa Xaa Cys Xaa Xaa Xaa Xaa Xaa Xaa Xaa Xaa Cys
        35                  40                  45

Xaa Xaa Xaa Lys Xaa Xaa Arg Xaa Xaa Cys Xaa Xaa Cys Arg Xaa Xaa
    50                  55                  60

Lys Cys Xaa Xaa Xaa Gly Met
65                  70

<210> SEQ ID NO 2
<211> LENGTH: 5
<212> TYPE: PRT
<213> ORGANISM: Artificial Sequence
<220> FEATURE:
<221> NAME/KEY: misc_feature
<223> OTHER INFORMATION: P-box ecdysone receptor domain sequence

<400> SEQUENCE: 2

Glu Gly Cys Lys Gly
1               5

<210> SEQ ID NO 3
<211> LENGTH: 5
<212> TYPE: PRT
<213> ORGANISM: Artificial Sequence
<220> FEATURE:
<221> NAME/KEY: misc_feature
<223> OTHER INFORMATION: Modified ecdysone receptor domain sequence
```

```
<400> SEQUENCE: 3

Gly Ser Cys Lys Val
1               5

<210> SEQ ID NO 4
<211> LENGTH: 13
<212> TYPE: DNA
<213> ORGANISM: Artificial Sequence
<220> FEATURE:
<221> NAME/KEY: misc_feature
<223> OTHER INFORMATION: Modified ecdysone response element
<221> NAME/KEY: misc_feature
<222> LOCATION: (1)..(13)
<223> OTHER INFORMATION: n is either g, c, t, or a

<400> SEQUENCE: 4
rgbnnmntgn ncy                                                        13

<210> SEQ ID NO 5
<211> LENGTH: 13
<212> TYPE: DNA
<213> ORGANISM: Artificial Sequence
<220> FEATURE:
<221> NAME/KEY: misc_feature
<223> OTHER INFORMATION: Modified ecdysone response element
<221> NAME/KEY: misc_feature
<222> LOCATION: (1)..(13)
<223> OTHER INFORMATION: n is either g, t, c, or a

<400> SEQUENCE: 5
rgnncanknn vcy                                                        13

<210> SEQ ID NO 6
<211> LENGTH: 13
<212> TYPE: DNA
<213> ORGANISM: Artificial Sequence
<220> FEATURE:
<221> NAME/KEY: misc_feature
<223> OTHER INFORMATION: Modified ecdysone response element
<221> NAME/KEY: misc_feature
<222> LOCATION: (7)..(7)
<223> OTHER INFORMATION: n is either g, t, c, or a

<400> SEQUENCE: 6
agtgcantgt tct                                                        13

<210> SEQ ID NO 7
<211> LENGTH: 13
<212> TYPE: DNA
<213> ORGANISM: Artificial Sequence
<220> FEATURE:
<221> NAME/KEY: misc_feature
<223> OTHER INFORMATION: Modified ecdysone response element
<221> NAME/KEY: misc_feature
<222> LOCATION: (1)..(13)
<223> OTHER INFORMATION: n is either g, t, c, or a

<400> SEQUENCE: 7
rgbnnmnrgb nnm                                                        13

<210> SEQ ID NO 8
<211> LENGTH: 49
<212> TYPE: DNA
<213> ORGANISM: Artificial Sequence
<220> FEATURE:
<221> NAME/KEY: misc_feature
<223> OTHER INFORMATION: Plasmid CMX-VpEcR

<400> SEQUENCE: 8
```
tacaacgccc tcacctgtgg atcctgcaag gtgtttcttt cgacgcagc                49

<210> SEQ ID NO 9
<211> LENGTH: 53
<212> TYPE: DNA
<213> ORGANISM: Artificial Sequence
<220> FEATURE:
<221> NAME/KEY: misc_feature
<223> OTHER INFORMATION: Annealed oligonucleotide containing HSP-EcRE

<400> SEQUENCE: 9
gtactcccgg ggcggggcta tgcggggcgg ggctaatcgc taggggcggg gca          53

<210> SEQ ID NO 10
<211> LENGTH: 53
<212> TYPE: DNA
<213> ORGANISM: Artificial Sequence
<220> FEATURE:
<221> NAME/KEY: misc_feature
<223> OTHER INFORMATION: Annealed oligonucleotide containing HSP-EcRE

<400> SEQUENCE: 10
gtactgcccc gcccctagcg attagccccg ccccgcatag ccccgccccg gga          53

<210> SEQ ID NO 11
<211> LENGTH: 34
<212> TYPE: DNA
<213> ORGANISM: Artificial Sequence
<220> FEATURE:
<221> NAME/KEY: misc_feature
<223> OTHER INFORMATION: Annealed oligonucleotide for
      E/GREx4-deltaMTV-Luc construct

<400> SEQUENCE: 11
agctcgatgg acaagtgcat tgttctttgc tgaa                               34

<210> SEQ ID NO 12
<211> LENGTH: 35
<212> TYPE: DNA
<213> ORGANISM: Artificial Sequence
<220> FEATURE:
<221> NAME/KEY: misc_feature
<223> OTHER INFORMATION: Annealed oligonucleotide for
      E/GREx4-deltaMTV-Luc construct

<400> SEQUENCE: 12
agctttcagc aagagaacaa tgcacttgtc catcg                              35

<210> SEQ ID NO 13
<211> LENGTH: 12
<212> TYPE: DNA
<213> ORGANISM: Artificial Sequence
<220> FEATURE:
<221> NAME/KEY: misc_feature
<223> OTHER INFORMATION: Modified ecdysone response element
<221> NAME/KEY: misc_feature
<222> LOCATION: (1)..(12)
<223> OTHER INFORMATION: n is either g, c, t, or a

<400> SEQUENCE: 13
rgbnnmtgnn cy                                                       12

<210> SEQ ID NO 14
<211> LENGTH: 14
<212> TYPE: DNA
<213> ORGANISM: Artificial Sequence
<220> FEATURE:

```
<221> NAME/KEY: misc_feature
<223> OTHER INFORMATION: Modified ecdysone response element
<221> NAME/KEY: misc_feature
<222> LOCATION: (1)..(14)
<223> OTHER INFORMATION: n is either g, c, t, or a

<400> SEQUENCE: 14 rgbnmnntg nncy                                                              14

<210> SEQ ID NO 15
<211> LENGTH: 15
<212> TYPE: DNA
<213> ORGANISM: Artificial Sequence
<220> FEATURE:
<221> NAME/KEY: misc_feature
<223> OTHER INFORMATION: Modified ecdysone response element
<221> NAME/KEY: misc_feature
<222> LOCATION: (1)..(15)
<223> OTHER INFORMATION: n is either g, c, t, or a

<400> SEQUENCE: 15
rgbnmmnnnt gnncy                                                            15

<210> SEQ ID NO 16
<211> LENGTH: 16
<212> TYPE: DNA
<213> ORGANISM: Artificial Sequence
<220> FEATURE:
<221> NAME/KEY: misc_feature
<223> OTHER INFORMATION: Modified ecdysone response element
<221> NAME/KEY: misc_feature
<222> LOCATION: (1)..(16)
<223> OTHER INFORMATION: n is either g, c, t, or a

<400> SEQUENCE: 16
rgbnmmnnnn tgnncy                                                           16

<210> SEQ ID NO 17
<211> LENGTH: 17
<212> TYPE: DNA
<213> ORGANISM: Artificial Sequence
<220> FEATURE:
<221> NAME/KEY: misc_feature
<223> OTHER INFORMATION: Modified ecdysone response element
<221> NAME/KEY: misc_feature
<222> LOCATION: (1)..(17)
<223> OTHER INFORMATION: n is either g, c, t, or a

<400> SEQUENCE: 17
rgbnmmnnnn ntgnncy                                                          17

<210> SEQ ID NO 18
<211> LENGTH: 12
<212> TYPE: DNA
<213> ORGANISM: Artificial Sequence
<220> FEATURE:
<221> NAME/KEY: misc_feature
<223> OTHER INFORMATION: Modified ecdysone response element
<221> NAME/KEY: misc_feature
<222> LOCATION: (1)..(12)
<223> OTHER INFORMATION: n is either g, c, t, or a

<400> SEQUENCE: 18
rgnncaknnv cy                                                               12

<210> SEQ ID NO 19
<211> LENGTH: 14
<212> TYPE: DNA
<213> ORGANISM: Artificial Sequence
```

```
<220> FEATURE:
<221> NAME/KEY: misc_feature
<223> OTHER INFORMATION: Modified ecdysone response element
<221> NAME/KEY: misc_feature
<222> LOCATION: (1)..(14)
<223> OTHER INFORMATION: n is either g, c, t, or a

<400> SEQUENCE: 19
rgnncannkn nvcy                                                           14

<210> SEQ ID NO 20
<211> LENGTH: 15
<212> TYPE: DNA
<213> ORGANISM: Artificial Sequence
<220> FEATURE:
<221> NAME/KEY: misc_feature
<223> OTHER INFORMATION: Modified ecdysone response element
<221> NAME/KEY: misc_feature
<222> LOCATION: (1)..(15)
<223> OTHER INFORMATION: n is either g, c, t, or a

<400> SEQUENCE: 20
rgnncannnk nnvcy                                                          15

<210> SEQ ID NO 21
<211> LENGTH: 16
<212> TYPE: DNA
<213> ORGANISM: Artificial Sequence
<220> FEATURE:
<221> NAME/KEY: misc_feature
<223> OTHER INFORMATION: Modified ecdysone response element
<221> NAME/KEY: misc_feature
<222> LOCATION: (1)..(16)
<223> OTHER INFORMATION: n is either g, c, t, or a

<400> SEQUENCE: 21
rgnncannnn knnvcy                                                         16

<210> SEQ ID NO 22
<211> LENGTH: 17
<212> TYPE: DNA
<213> ORGANISM: Artificial Sequence
<220> FEATURE:
<221> NAME/KEY: misc_feature
<223> OTHER INFORMATION: Modified ecdysone response element
<221> NAME/KEY: misc_feature
<222> LOCATION: (1)..(17)
<223> OTHER INFORMATION: n is either g, c, t, or a

<400> SEQUENCE: 22
rgnncannnn nknnvcy                                                        17

<210> SEQ ID NO 23
<211> LENGTH: 12
<212> TYPE: DNA
<213> ORGANISM: Artificial Sequence
<220> FEATURE:
<221> NAME/KEY: misc_feature
<223> OTHER INFORMATION: Modified ecdysone response element
<221> NAME/KEY: misc_feature
<222> LOCATION: (1)..(12)
<223> OTHER INFORMATION: n is either g, c, t, or a

<400> SEQUENCE: 23
rgbnnmrgbn nm                                                             12

<210> SEQ ID NO 24
<211> LENGTH: 14
<212> TYPE: DNA
```

```
<213> ORGANISM: Artificial Sequence
<220> FEATURE:
<221> NAME/KEY: misc_feature
<223> OTHER INFORMATION: Modified ecdysone response element
<221> NAME/KEY: misc_feature
<222> LOCATION: (1)..(14)
<223> OTHER INFORMATION: n is either g, c, t, or a

<400> SEQUENCE: 24
rgbnnmnnrg bnnm                                                14

<210> SEQ ID NO 25
<211> LENGTH: 15
<212> TYPE: DNA
<213> ORGANISM: Artificial Sequence
<220> FEATURE:
<221> NAME/KEY: misc_feature
<223> OTHER INFORMATION: Modified ecdysone response element
<221> NAME/KEY: misc_feature
<222> LOCATION: (1)..(15)
<223> OTHER INFORMATION: n is either g, c, t, or a

<400> SEQUENCE: 25
rgbnnmnnnr gbnnm                                               15

<210> SEQ ID NO 26
<211> LENGTH: 16
<212> TYPE: DNA
<213> ORGANISM: Artificial Sequence
<220> FEATURE:
<221> NAME/KEY: misc_feature
<223> OTHER INFORMATION: Modified ecdysone response element
<221> NAME/KEY: misc_feature
<222> LOCATION: (1)..(16)
<223> OTHER INFORMATION: n is either g, c, t, or a

<400> SEQUENCE: 26
rgbnnmnnnn rgbnnm                                              16

<210> SEQ ID NO 27
<211> LENGTH: 17
<212> TYPE: DNA
<213> ORGANISM: Artificial Sequence
<220> FEATURE:
<221> NAME/KEY: misc_feature
<223> OTHER INFORMATION: Modified ecdysone response element
<221> NAME/KEY: misc_feature
<222> LOCATION: (1)..(17)
<223> OTHER INFORMATION: n is either g, c, t, or a

<400> SEQUENCE: 27
rgbnnmnnnn nrgbnnm                                             17
```